US008864709B2

(12) United States Patent
Akagane et al.

(10) Patent No.: US 8,864,709 B2
(45) Date of Patent: Oct. 21, 2014

(54) MEDICAL LIQUID SUPPLY DEVICE

(71) Applicant: Olympus Medical Systems Corp., Tokyo (JP)

(72) Inventors: Tsunetaka Akagane, Hachioji (JP); Satoshi Honma, Hino (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 13/659,535

(22) Filed: Oct. 24, 2012

(65) Prior Publication Data
US 2013/0324917 A1 Dec. 5, 2013
Related U.S. Application Data

(63) Continuation of application No. PCT/JP2012/056279, filed on Mar. 12, 2012.

(60) Provisional application No. 61/453,727, filed on Mar. 17, 2011.

(51) Int. Cl.
*A61M 1/00* (2006.01)
*A61B 17/20* (2006.01)
*A61M 3/00* (2006.01)
*A61B 17/32* (2006.01)
*A61M 3/02* (2006.01)
*A61B 18/14* (2006.01)
*A61B 18/00* (2006.01)

(52) U.S. Cl.
CPC .... *A61M 3/0283* (2013.01); *A61B 2018/00744* (2013.01); *A61B 17/320068* (2013.01); *A61B 2018/00642* (2013.01); *A61B 17/320092* (2013.01); *A61B 2218/007* (2013.01); *A61B 2018/00994* (2013.01); *A61B 2217/005* (2013.01); *A61B 2217/007* (2013.01); *A61B 2018/00863* (2013.01); *A61M 1/0058* (2013.01); *A61B 2218/002* (2013.01); *A61B 18/1445* (2013.01)
USPC .................. 604/118; 604/22; 604/43; 604/35

(58) Field of Classification Search
CPC  A61M 1/0058; A61M 1/0062; A61M 1/0064
USPC .............. 604/27, 30, 35, 39, 43, 118, 119, 22
See application file for complete search history.

(56) References Cited

U.S. PATENT DOCUMENTS 3,805,787 A   4/1974   Banko
6,322,533 B1  11/2001  Gonon
(Continued)

FOREIGN PATENT DOCUMENTS

DE   20 2008 000 276 U1   6/2008
EP   0 537 573 A2          4/1993
(Continued)

OTHER PUBLICATIONS

Apr. 10, 2012 International Search Report issued in International Patent Application No. PCT/JP2012/056279.
Sep. 26, 2013 International Preliminary Report on Patentability International Application No. PCT/JP2012/056279.
Extended European Search Report issued in European Patent Application No. 12758080.1 dated Dec. 20, 2013.

*Primary Examiner* — Theodore Stigell
*Assistant Examiner* — Benjamin Koo
(74) *Attorney, Agent, or Firm* — Oliff PLC

(57) ABSTRACT

In a medical liquid supply device, a control unit controls a liquid supply driver so that a liquid flows from the liquid supply driver in a liquid supply path regardless of whether a liquid-supply ON mode is selected. All of the liquid flowing from the liquid supply driver flows into a communication path when the liquid-supply ON mode is not selected. At least a part of the liquid flowing from the liquid supply driver does not flow into the communication path and is thereby supplied from a distal end of the liquid supply path when the liquid-supply ON mode is selected.

8 Claims, 13 Drawing Sheets

(56) References Cited

U.S. PATENT DOCUMENTS

| | | |
|---|---|---|
| 7,025,755 B2 | 4/2006 | Epstein |
| 7,169,123 B2 * | 1/2007 | Kadziauskas et al. .......... 604/22 |
| 2003/0078644 A1 | 4/2003 | Phan |
| 2003/0225403 A1 | 12/2003 | Woloszko et al. |
| 2006/0258975 A1 | 11/2006 | Takahashi |
| 2008/0167645 A1 | 7/2008 | Woloszko |
| 2012/0215221 A1 | 8/2012 | Woloszko |

FOREIGN PATENT DOCUMENTS

| | | |
|---|---|---|
| FR | 2 780 268 | 12/1999 |
| JP | A-05-023345 | 2/1993 |
| JP | A-09-140722 | 6/1997 |
| JP | A-2005-027809 | 2/2005 |
| JP | A-2005-506872 | 3/2005 |

* cited by examiner

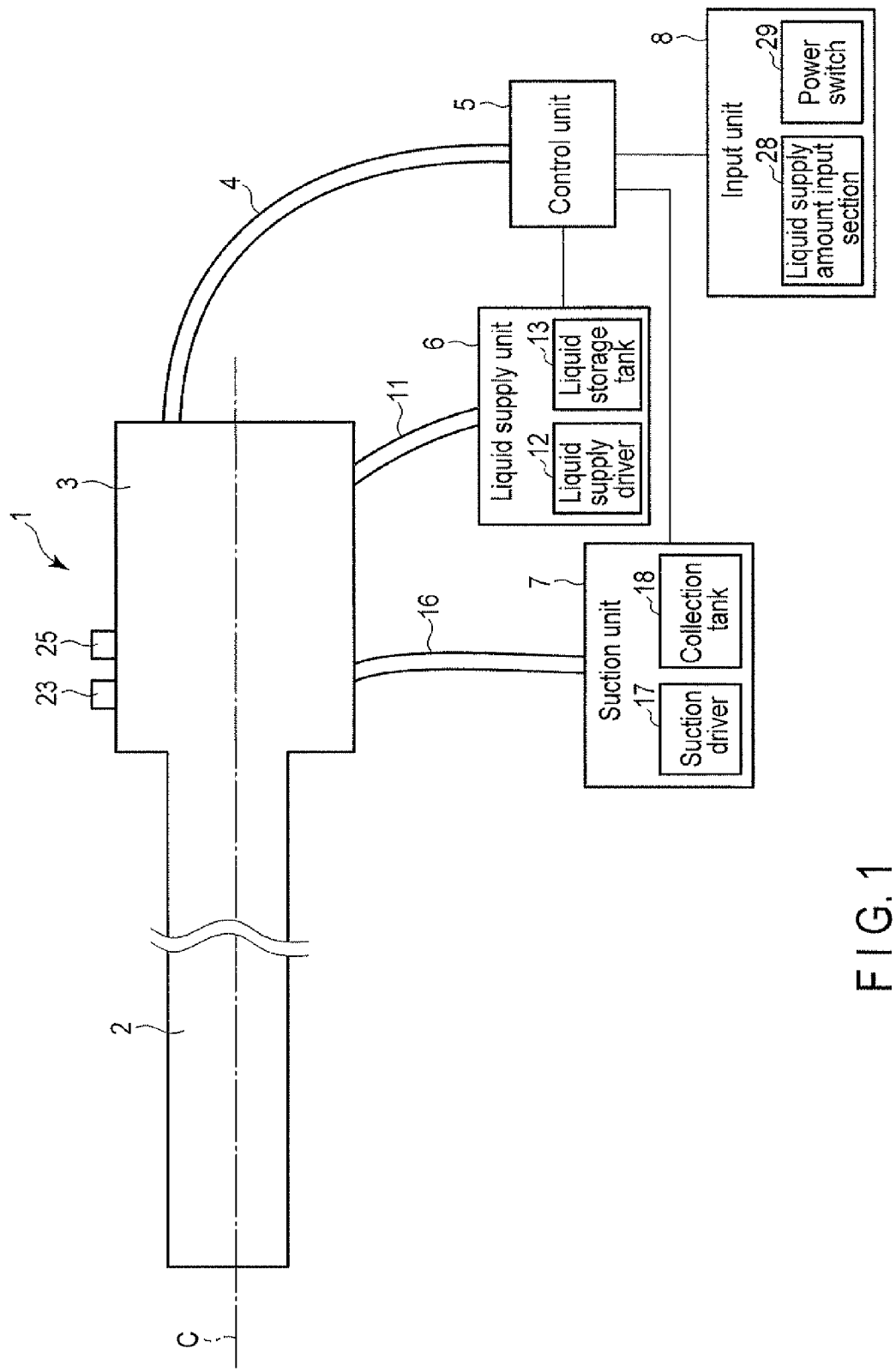
F I G. 1

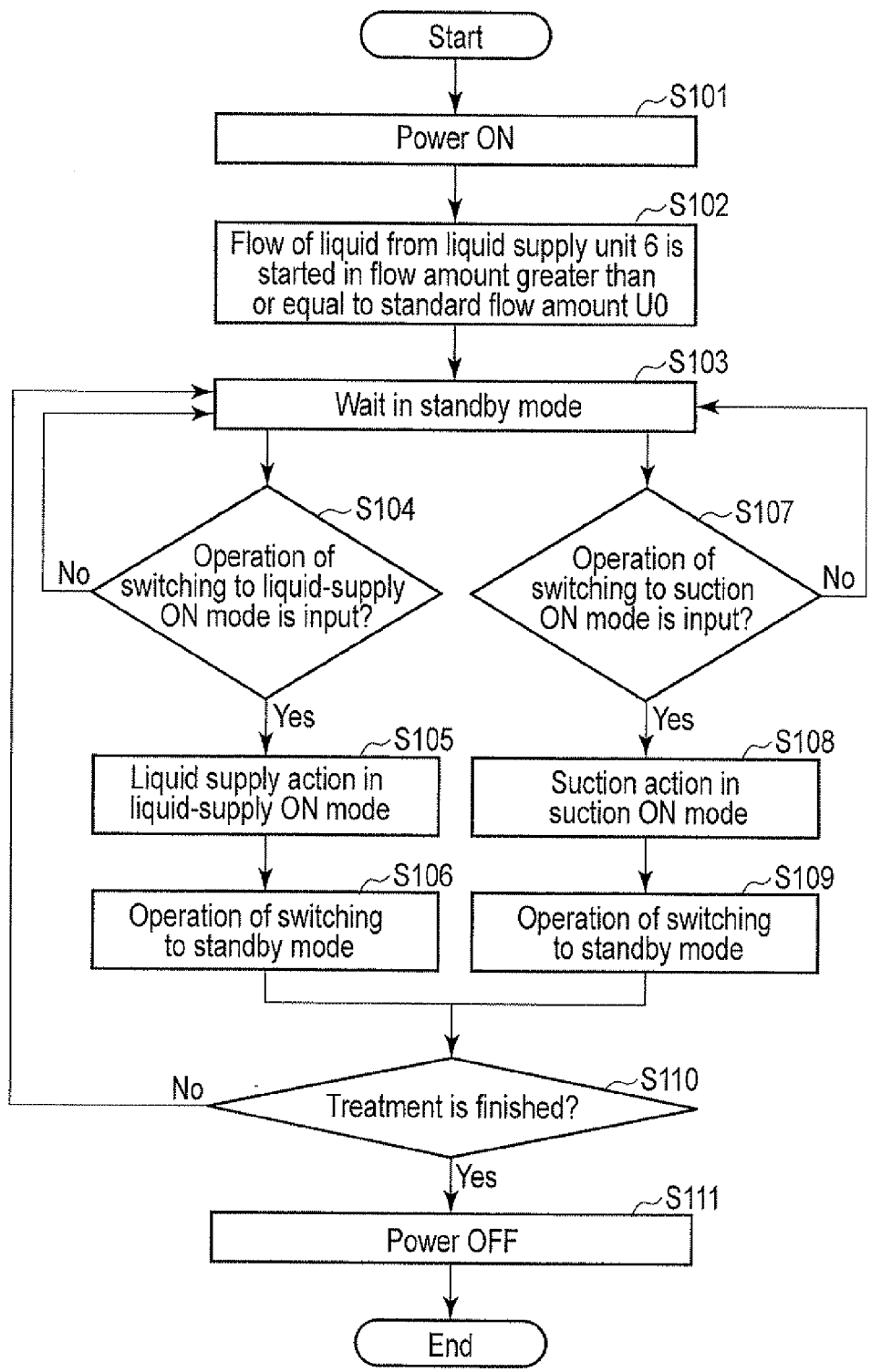
F I G. 3

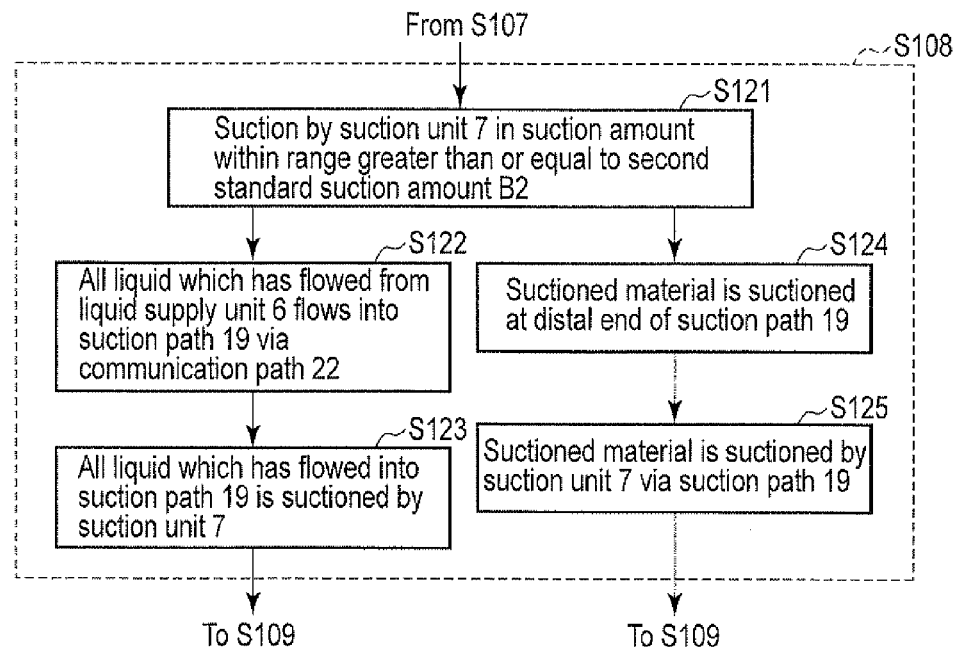
F I G. 8
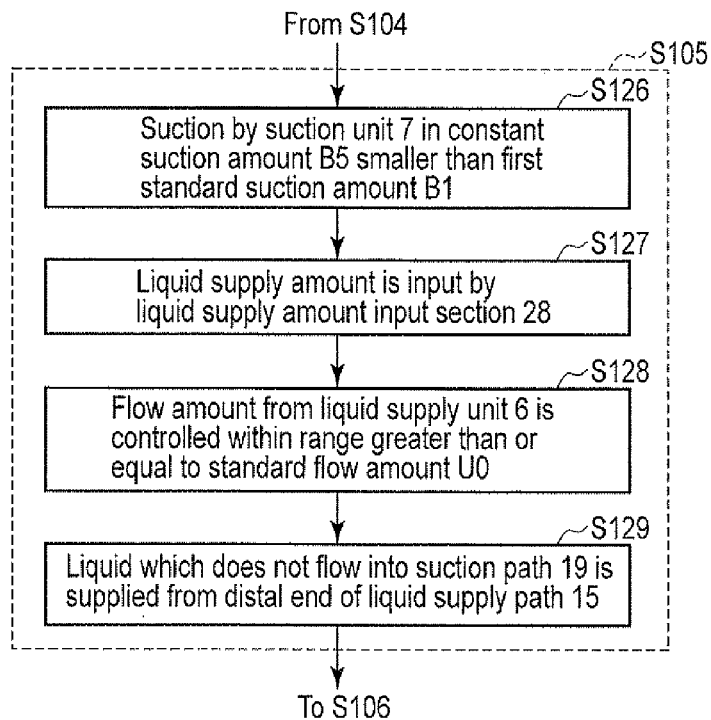
F I G. 9

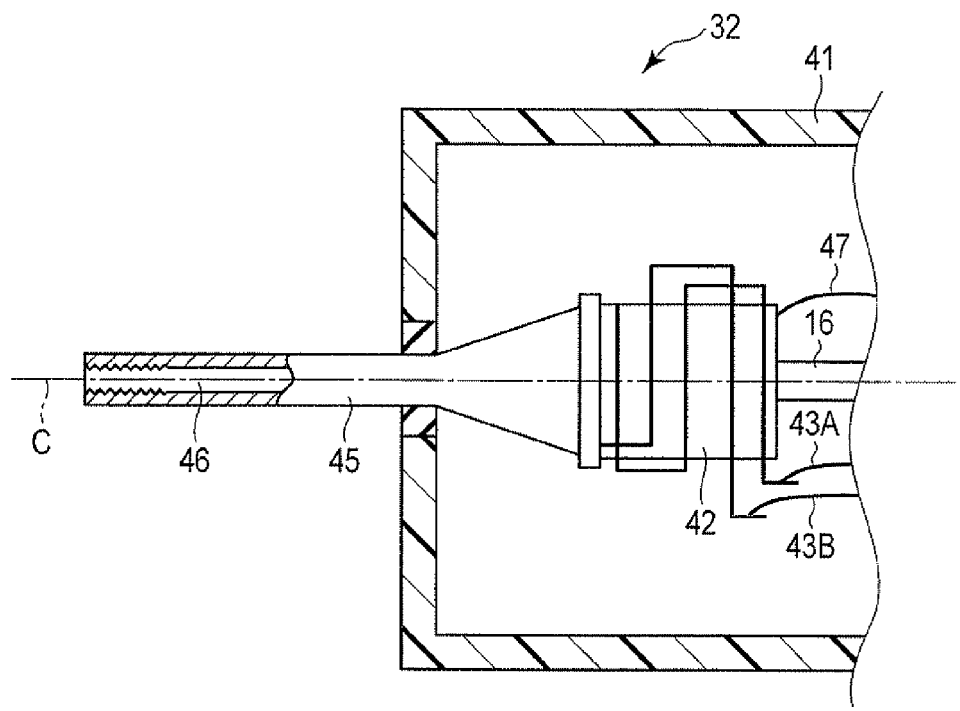
F I G. 12
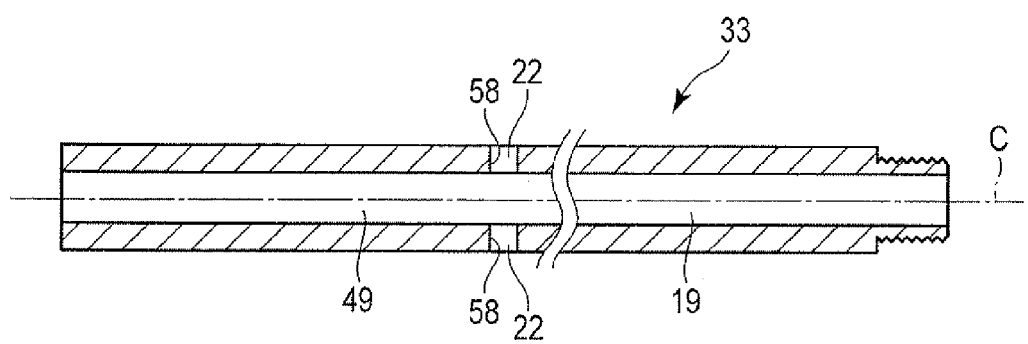
F I G. 13

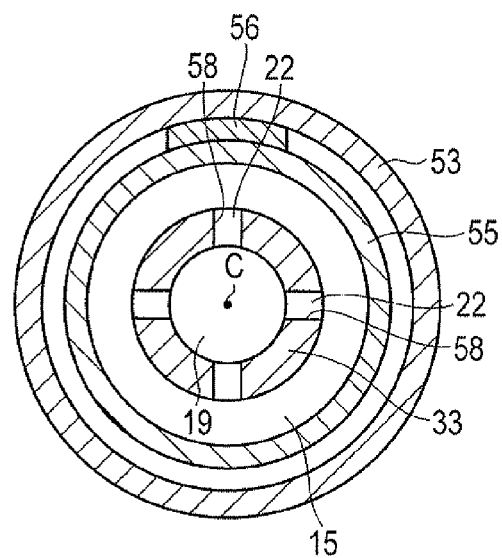
F I G. 16
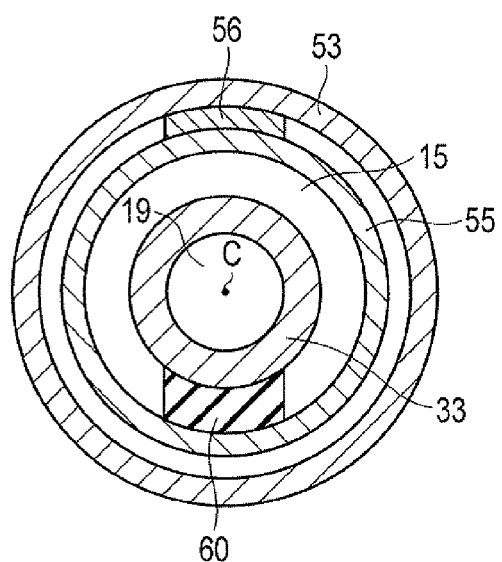
F I G. 17

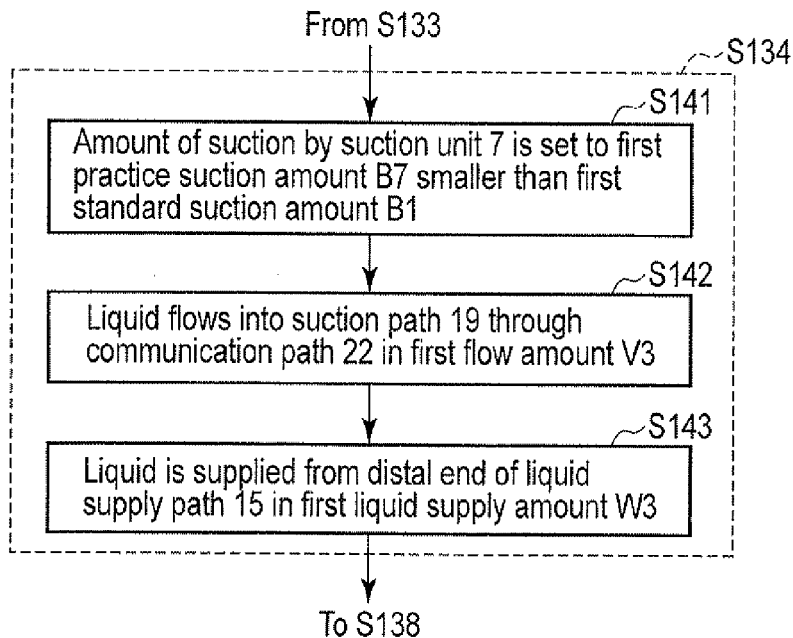
F I G. 20
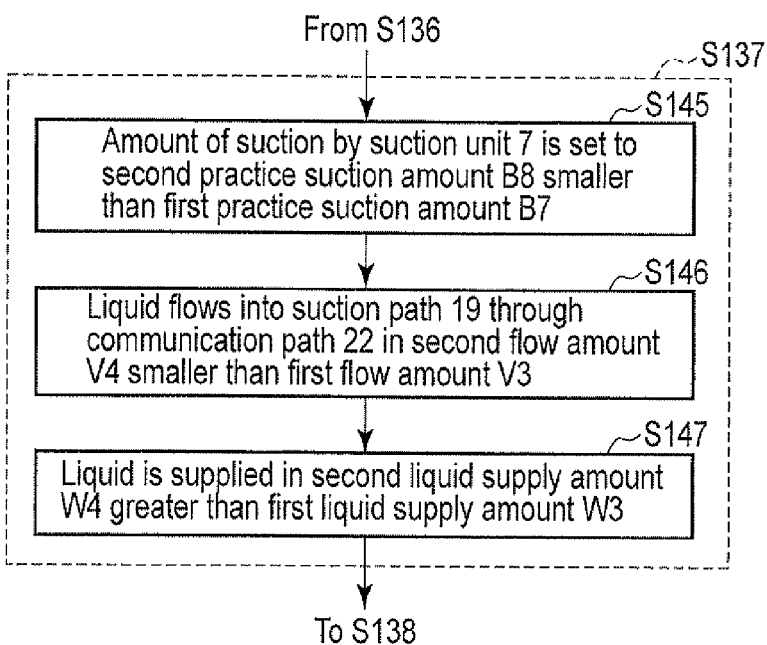
F I G. 21

MEDICAL LIQUID SUPPLY DEVICE

CROSS-REFERENCE TO RELATED APPLICATIONS

This is a Continuation application of PCT Application No. PCT/JP2012/056279, filed Mar. 12, 2012 and based upon and claiming the benefit of priority from prior U.S. Provisional Application No. 61/453,727, filed Mar. 17, 2011, the entire contents of which are incorporated herein by reference.

BACKGROUND OF THE INVENTION

1. Field of the Invention

The present invention relates to a medical liquid supply device used in a treatment of, for example, living tissue.

2. Description of the Related Art

Jpn. Pat. Appln. KOKAI Publication No. 2005-27809 has disclosed an ultrasonic treatment device configured to conduct a treatment known as ultrasonic suction and a treatment known as ultrasonic coagulation-and-cutting. In the ultrasonic suction treatment, a liquid is generally supplied to efficiently shatter and emulsify living tissue. A physical phenomenon known as cavitation is efficiently caused by the liquid supply. More specifically, as an ultrasonic probe repeats tens of thousands of high-velocity vibrations per second by ultrasonic vibrations, pressure periodically varies in a vicinity of a distal face of the ultrasonic probe. When the pressure in the vicinity of the distal face is lower than saturated vapor pressure for only a short time due to a pressure variation, small air bubbles (cavities) are generated in a liquid supplied from the ultrasonic treatment device to a vicinity of a treatment position of the living tissue. The generated air bubbles disappear due to force that acts when the pressure in the vicinity of the distal face increases (compression). The above-described physical phenomenon is called a cavitation phenomenon. An inelastic living tissue such as a hepatic cell is shattered and emulsified by impact energy when the air bubbles disappear. Thus, it is necessary to supply a liquid to the vicinity of the treatment position when the ultrasonic suction is conducted. In this ultrasonic treatment device, a clearance between an outer peripheral portion of the probe and an inner peripheral portion of a sheath is a liquid supply path. A liquid is supplied from a distal end of the liquid supply path (sheath) to, for example, living tissue. The liquid is supplied to the liquid supply path between the probe and the sheath via an elongated tube connected to a liquid supply unit.

Jpn. Pat. Appln. KOKAI Publication No. 5-23345 has disclosed an ultrasonic treatment device having a function for supplying a perfusion liquid. In this ultrasonic treatment device, a liquid supply path of the perfusion liquid is formed between a sheath and a probe. A suction path is formed inside the probe. The probe is provided with a communication hole configured to allow communication between the liquid supply path and the suction path. The perfusion liquid is discharged from the liquid supply path through the communication hole and the suction path in order. The liquid is supplied to the liquid supply path between the probe and the sheath via an elongated tube connected to a liquid supply unit.

BRIEF SUMMARY OF THE INVENTION

According to one aspect of the invention, a medical liquid supply device includes a first path defining portion which defines a liquid supply path; a second path defining portion which defines a suction path; a third path defining portion which defines a communication path configured to allow communication between the liquid supply path and the suction path; a liquid supply unit to which a proximal end of the first path defining portion is connected, and which is configured to cause a liquid to flow into the liquid supply path in a flow amount greater than or equal to a standard flow amount so that the liquid supply path constantly has no parts lacking the liquid up to the communication path in a liquid supply direction; a suction unit to which a proximal end of the second path defining portion is connected, and which is configured to perform suction via the suction path; a liquid supply mode input section configured to switch a liquid supply mode between a liquid-supply ON mode in which the liquid is supplied from a distal end of the liquid supply path and a liquid-supply OFF mode in which the liquid is not supplied from the distal end of the liquid supply path; and a control unit which is configured to control an amount of suction by the suction unit in accordance with a switching operation in the liquid supply mode input section to adjust a flow amount of the liquid flowing from the liquid supply path into the suction path via the communication path between the liquid-supply ON mode and the liquid-supply OFF mode.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1 is a schematic diagram showing a medical liquid supply device according to a first embodiment of the present invention;

FIG. 3 is a flowchart illustrating an action of the medical liquid supply device according to the first embodiment;

FIG. 8 is a flowchart illustrating a suction action of the medical liquid supply device according to the first embodiment in a suction ON mode;

FIG. 9 is a flowchart illustrating a liquid supply action of a medical liquid supply device according to a first modification of the first embodiment in the liquid-supply ON mode;

FIG. 12 is a schematic sectional view showing a configuration of a vibration unit of the medical treatment according to the second embodiment;

FIG. 13 is a schematic sectional view showing a configuration of an ultrasonic probe of the medical treatment device according to the second embodiment;

FIG. 16 is a sectional view taken along line 16-16 of FIG. 14;

FIG. 17 is a sectional view taken along line 17-17 of FIG. 14;

FIG. 20 is a flowchart illustrating a liquid supply action of the medical treatment device according to the second embodiment in a first liquid supply mode;

FIG. 21 is a flowchart illustrating a liquid supply action of the medical treatment device according to the second embodiment in a second liquid supply mode;

DETAILED DESCRIPTION OF THE INVENTION

First Embodiment

Figure 2:
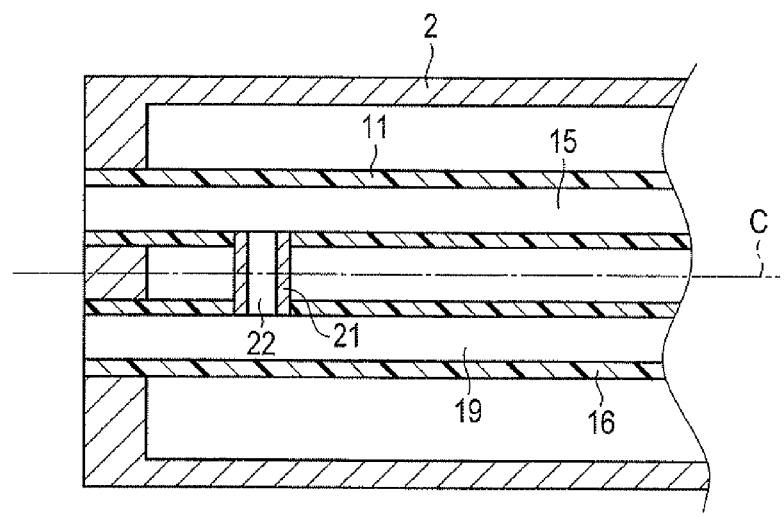
FIG. 2 is a schematic sectional view showing an internal configuration of an insertion section of the medical liquid supply device according to the first embodiment.

A first embodiment of the present invention is described with reference to FIG. 1 to FIG. 8. FIG. 1 is a diagram showing a medical liquid supply device 1 according to the present embodiment. As shown in FIG. 1, the medical liquid supply device 1 includes an insertion section 2 configured to be inserted into a body cavity, and a holding section 3 provided to a proximal direction side of the insertion section 2. The insertion section 2 is elongated along a longitudinal axis C. One end of a cable 4 is connected to the holding section 3. The other end of the cable 4 is connected to a control unit 5. The control unit 5 is electrically connected to a liquid supply unit 6, a suction unit 7, and an input unit 8.

FIG. 2 is a diagram showing an internal configuration of the insertion section 2. As shown in FIG. 2, a liquid supply tube 11 extends along the longitudinal axis C inside the insertion section 2. A distal end of the liquid supply tube 11 extends to a distal end of the insertion section 2. As shown in FIG. 1, a proximal end of the liquid supply tube 11 is connected to the liquid supply unit 6 through an inside of the holding section 3.

The liquid supply unit 6 includes a liquid supply driver 12, and a liquid storage tank 13 configured to store a liquid such as a physiological saline solution to be supplied. A liquid supply path 15, through which the liquid flowing from the liquid supply unit 6 is passed, is defined by the liquid supply tube 11. That is, the liquid supply tube 11 serves as a first path defining portion which defines the liquid supply path 15.

As shown in FIG. 2, a suction tube 16 extends along the longitudinal axis C inside the insertion section 2. A distal end of the suction tube 16 extends to the distal end of the insertion section 2. As shown in FIG. 1, a proximal end of the suction tube 16 is connected to the suction unit 7 through the inside of the holding portion 3. The suction unit 7 includes a suction driver 17, and a collection tank 18 configured to collect suctioned material, such as living tissue, and a liquid suctioned by the suction unit 7. A suction path 19, through which the suctioned material and the liquid to the suction unit 7 is passed, is defined by the suction path 19. That is, the suction tube 16 serves as a second path defining portion which defines the suction path 19.

As shown in FIG. 2, a cylindrical intermediary member 21 is provided in a distal portion of the insertion section 2. The intermediary member 21 has one end connected to the liquid supply tube 11, and the other end connected to the suction tube 16. A communication path 22 configured to allow communication between a distal portion of the liquid supply path 15 and a distal portion of the suction path 19 is defined by the intermediary member 21. That is, the intermediary member 21 serves as a third path defining portion which defines the communication path 22.

As shown in FIG. 1, a liquid supply mode input switch 23, which is a liquid supply mode input section, and a suction mode input switch 25, which is a suction mode input section, are provided on an outer peripheral portion of the holding section 3. The liquid supply mode input switch 23 and the suction mode input switch 25 are electrically connected to the control unit 5 via an electrical signal line (not shown) which passes through an inside of the cable 4. The liquid supply mode is switched by the liquid supply mode input switch 23 between a liquid-supply ON mode in which a liquid is supplied from the distal end of the liquid supply path 15 and a liquid-supply OFF mode in which the liquid is not supplied from the distal end of the liquid supply path 15. The suction mode is switched by the suction mode input switch 25 in the liquid-supply OFF mode between a suction ON mode in which suction from the distal end of the suction path 19 is performed and a standby mode in which suction from the distal end of the suction path 19 is not performed. A switching operation of the suction mode by the suction mode input switch 25 is only input to the control unit 5 in the liquid-supply OFF mode. In the liquid-supply ON mode, a condition is controlled such that the suctioned material such as living tissue is not suctioned from the distal end of the suction path 19.

The input unit 8 is, for example, a foot switch or a remote switch. The input unit 8 includes a liquid supply amount input section 28 configured to input a liquid supply amount from the distal end of the liquid supply path 15 in the liquid-supply ON mode, and a power switch 29 of the medical liquid supply device 1.

Now, the functions of the medical liquid supply device 1 are described. FIG. 3 is a flowchart illustrating an action of the medical liquid supply device 1. As shown in FIG. 3, in order to conduct a treatment by the medical liquid supply device 1, the medical liquid supply device 1 is powered ON by the power switch 29 of the input unit 8 (step S101).

When the power is turned ON, the liquid supply driver 12 of the liquid supply unit 6 is driven. As a result, the liquid in the liquid storage tank 13 flows from the liquid supply unit 6 to the liquid supply path 15. At the same time, the flow of the liquid from the liquid supply unit 6 is started in a flow amount greater than or equal to a standard flow amount U0 per second (step S102). When the liquid flows in the flow amount greater than or equal to the standard flow amount U0, the liquid supply path 15 constantly has no parts lacking the liquid up to the communication path 22 in a liquid supply direction.

Figure 4:
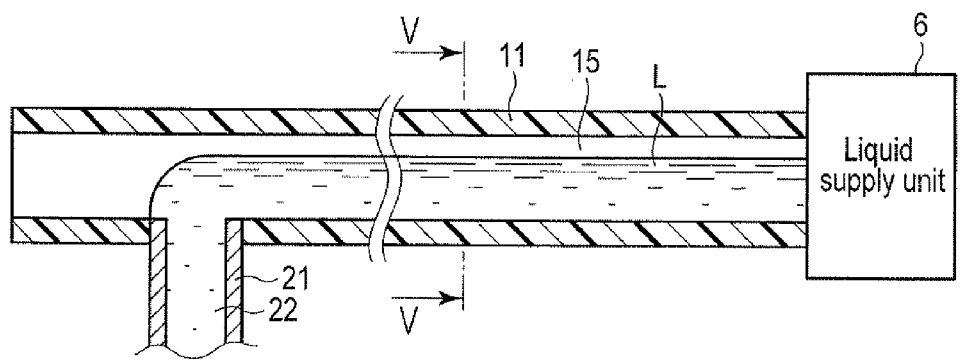
FIG. 4 is a schematic sectional view showing one condition of a liquid supply path during a treatment by the medical liquid supply device according to the first embodiment.
Figure 5:
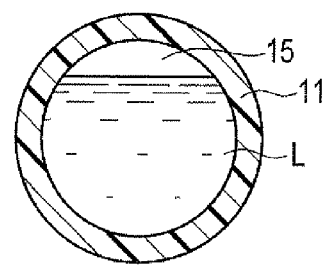
FIG. 5 is a sectional view taken along line V-V of FIG. 4.

FIG. 4 and FIG. 5 are views showing one condition of the liquid supply path 15 during a treatment by the medical liquid supply device 1. As shown in FIG. 4, during the treatment by the medical liquid supply device 1, the liquid supply path 15 constantly has no parts lacking the liquid L up to the communication path 22 in the liquid supply direction. That is, the liquid L constantly continues from the proximal end of the liquid supply path 15 to the communication path 22 along the liquid supply direction. Here, when there are no parts lacking the liquid L in the liquid supply direction, the liquid L does not always have to occupy a whole cross sectional area of the liquid supply path 15 in a section perpendicular to the liquid supply direction. That is, as shown in FIG. 5, part of the cross sectional area of the liquid supply path 15 has only to be occupied by the liquid L in the section perpendicular to the liquid supply direction.

The control unit 5 then controls to set a condition to wait in the standby mode (step S103). The standby mode is the liquid-supply OFF mode in which the liquid is not supplied from the distal end of the liquid supply path 15 to, for example, living tissue. In the standby mode, the suctioned material such as living tissue is not suctioned from the distal end of the suction path 19.

Figure 6:
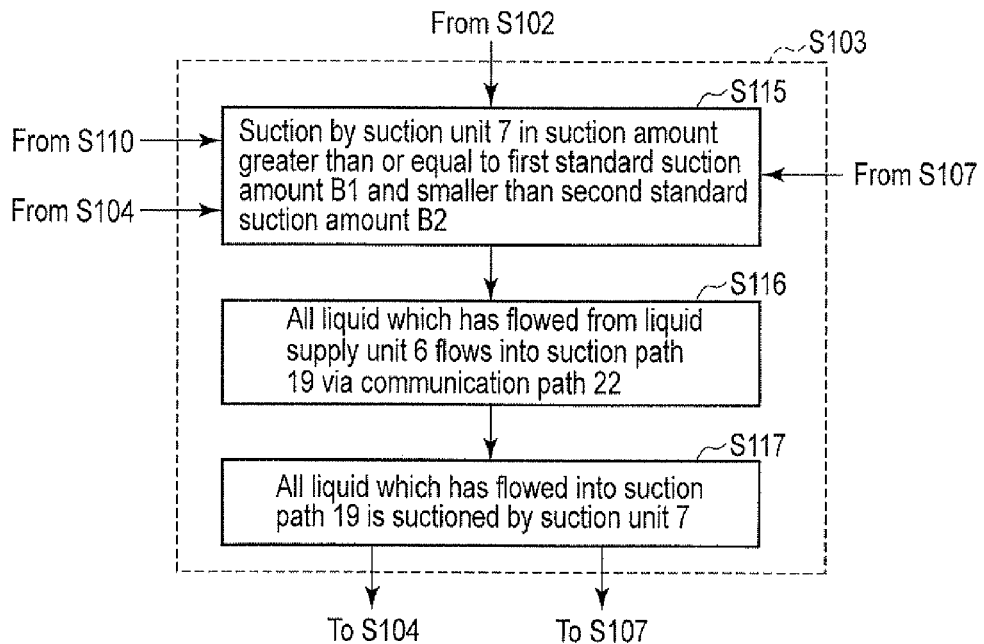
FIG. 6 is a flowchart illustrating an action of the medical liquid supply device according to the first embodiment when waiting in a standby mode.

FIG. 6 is a flowchart illustrating an action of the medical liquid supply device 1 when waiting in the standby mode. As shown in FIG. 6, in order to wait in the standby mode, the suction driver 17 of the suction unit 7 is first driven. In this case, the amount of suction by the suction unit 7 per second is set by the control unit 5 to a range greater than or equal to a first standard suction amount (standard suction amount) B1 and smaller than a second standard suction amount B2 (step S115). Here, the second standard suction amount B2 is greater than the first standard suction amount B1. The amount of suction by the suction unit 7 is smaller than the second standard suction amount B2, so that at the distal end of the suction path 19, suction force does not become great enough to be able to suction the suctioned material such as living tissue.

As the amount of suction by the suction unit 7 is controlled to be greater than or equal to the first standard suction amount B1, all the liquid, which has flowed from the liquid supply unit 6, flows into the suction path 19 via the communication path 22 (step S116). All the liquid, which has flowed into the suction path 19, is suctioned by the suction unit 7, and collected in the collection tank 18 (step S117). That is, all the liquid, which has flowed from the liquid supply unit 6, is suctioned by the suction unit 7 through the communication path 22 and the suction path 19 in order. Consequently, in the standby mode, the liquid is not supplied from the distal end of the liquid supply path 15, and the suctioned material is not suctioned from the distal end of the suction path 19.

When the liquid is supplied to, for example, living tissue from the standby state, the liquid supply mode is switched by the liquid supply mode input switch 23 as shown in FIG. 3 (step S104—Yes). In this way, the liquid supply mode is switched from the standby mode (liquid-supply OFF mode) in which the liquid is not supplied from the distal end of the liquid supply path 15 to the liquid-supply ON mode in which the liquid is supplied from the distal end of the liquid supply path 15. A liquid supply action in the liquid-supply ON mode is then performed (step S105).

Figure 7:
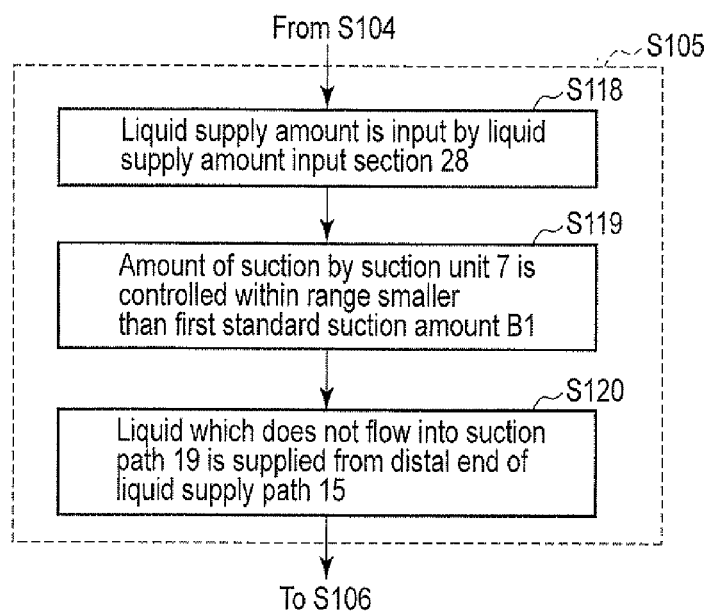
FIG. 7 is a flowchart illustrating a liquid supply action of the medical liquid supply device according to the first embodiment in a liquid-supply ON mode.

FIG. 7 is a flowchart illustrating the liquid supply action in the liquid-supply ON mode. As shown in FIG. 7, in order to supply the liquid in the liquid-supply ON mode, a liquid supply amount from the distal end of the liquid supply path 15 per second is input by the liquid supply amount input section 28 of the input unit 8 (step S118). In accordance with the input liquid supply amount, the amount of suction by the suction unit 7 per second is controlled by the control unit 5 within a range smaller than the first standard suction amount B1 (step S119). Here, the range smaller than the first standard suction amount B1 includes a case in which the suction driver 17 of the suction unit 7 is stopped and a suction force of the suction unit 7 is zero. In the liquid-supply ON mode, the amount of suction by the suction unit 7 is smaller than the first standard suction amount B1. Therefore, at least part of the liquid, which has flowed from the liquid supply unit 6, does not flow into the suction path 19 via the communication path 22. The liquid which does not flow into the suction path 19 is supplied to, for example, living tissue from the distal end of the liquid supply path 15 (step S120).

As described above, the control unit 5 controls the amount of suction by the suction unit 7 between the standby mode (liquid-supply OFF mode) and the liquid-supply ON mode in accordance with the switching operation in the liquid supply mode input switch 23. That is, the amount of suction by the suction unit 7 is greater than or equal to the first standard suction amount B1 in the standby mode (liquid-supply OFF mode), and the amount of suction by the suction unit 7 is smaller than the first standard suction amount B1 in the liquid-supply ON mode. Thus, in the standby mode (liquid-supply OFF mode), all the liquid, which has flowed from the liquid supply unit 6, flows into the suction path 19 via the communication path 22. On the other hand, in the liquid-supply ON mode, at least part of the liquid, which has flowed from the liquid supply unit 6, does not flow into the suction path 19 via the communication path 22. That is, the amount of suction by the suction unit 7 is controlled between the standby mode (liquid-supply OFF mode) and the liquid-supply ON mode to adjust a liquid flow amount of the liquid flowing into the suction path 19.

In the liquid-supply ON mode, the amount of suction by the suction unit 7 per second is controlled within the range smaller than the first standard suction amount B1. For example, the amount of suction by the suction unit 7 is set to a first practice suction amount B3 smaller than the first standard suction amount B1. In this case, the flow amount of the liquid flowing from the liquid supply unit 6 into the suction path 19 is a first flow amount V1, and the amount of the liquid supplied from the distal end of the liquid supply path 15 is a first liquid supply amount W1. The amount of suction by the suction unit 7 is increased from the first practice suction amount B3 to a second practice suction amount B4 within a range smaller than the first standard suction amount B1. As a result of the suction in the second practice suction amount B4, the flow amount of the liquid flowing from the liquid supply unit 6 into the suction path 19 reaches a second flow amount V2 greater than the first flow amount V1. The liquid supply amount of the liquid flowing from the liquid supply unit 6 and supplied from the distal end of the liquid supply path 15 is a second liquid supply amount W2 smaller than the first liquid supply amount W1. That is, in the liquid-supply ON mode, the amount of suction by the suction unit 7 is controlled within the range smaller than the first standard suction amount B1, and the flow amount of the liquid flowing from the liquid supply path 15 into the suction path 19 via the communication path 22 is thereby adjusted. Thus, the amount of the liquid supplied from the distal end of the liquid supply path 15 is adjusted.

In the medical liquid supply device 1, the liquid flows from the liquid supply unit 6 to the liquid supply path 15 in the flow amount per second greater than or equal to the standard flow amount U0 in the liquid-supply OFF mode including the standby mode as well. Therefore, the liquid supply path 15 constantly has no parts lacking the liquid up to the communication path 22 in the liquid supply direction in the liquid-supply OFF mode as well.

Here, suppose that the flow of the liquid from the liquid supply unit 6 to the liquid supply path 15 is started by an operation of switching to the liquid-supply ON mode in the liquid supply mode input switch 23. In this case, the liquid does not flow into the liquid supply path 15 from the liquid supply unit 6 in the liquid-supply OFF mode, so that the liquid supply path 15 has a part lacking the liquid in the liquid supply direction. Thus, even if the flow of the liquid from the liquid supply unit 6 to the liquid supply path 15 is started, it requires time before the liquid is supplied from the distal end of the liquid supply path 15. Accordingly, a response of the liquid supply from the distal end of the liquid supply path 15 deteriorates.

Here, A is a cross sectional area of the liquid supply path 15 perpendicular to the liquid supply direction, D is a dimension of the part lacking the liquid in the liquid supply direction, U1 is a flow amount from the liquid supply unit 6 per second, and T is a time from the start of the flow of the liquid from the liquid supply unit 6 to the start of the supply of the liquid from the distal end of the liquid supply path 15. Suppose that the liquid occupies the whole cross sectional area of the liquid supply path 15 in a section perpendicular to the liquid supply direction in parts other than the part lacking the liquid. In this case, the relationship $$T = A \cdot D / U1 \qquad (1)$$

is satisfied. For example, the time T is about four seconds if the cross sectional area A is 3.14 mm$^2$, the dimension of the part lacking the liquid is 50 mm, and the flow amount U1 is 40 mm$^3$ per second. That is, it requires about four seconds from the start of the flow of the liquid from the liquid supply unit 6 to the start of the supply of the liquid from the distal end of the liquid supply path 15.

When the liquid supply path 15 has the part lacking the liquid in the liquid supply direction, a constant amount of the liquid may not be supplied from the distal end of the liquid supply path 15 even after the flow of the liquid from the liquid supply unit 6 to the liquid supply path 15 is started. Accordingly, the stability of the liquid supply from the distal end of the liquid supply path 15 deteriorates.

In contrast, in the medical liquid supply device 1 according to the present embodiment, the liquid supply path 15 constantly has no parts lacking the liquid up to the communication path 22 in the liquid supply direction in the liquid-supply OFF mode as well. Therefore, the liquid can be stably supplied from the distal end of the liquid supply path 15 without the need for much time by the operation of switching to the liquid-supply ON mode in the liquid supply mode input switch 23. That is, the liquid is stably supplied from the distal end of the liquid supply path 15 with high response.

When the liquid supply action in the liquid-supply ON mode is completed, the operation of switching to the standby mode (liquid-supply OFF mode) is performed by the liquid supply mode input switch 23 as shown in FIG. 3 (step S106). The process then moves to step S110.

When, for example, living tissue is suctioned from the standby state, the suction mode is switched by the suction mode input switch 25 as shown in FIG. 3 (step S107—Yes). In this way, the suction mode is switched from the standby mode in which suction from the distal end of the suction path 19 is not performed to the suction ON mode in which suction from the distal end of the suction path 19 is performed. A suction action in the suction ON mode is then performed (step S108).

The operation of switching the suction mode in the suction mode input switch 25 is input to the control unit 5 in the liquid-supply OFF mode alone. As described above, in the liquid-supply ON mode, the condition is controlled such that the suctioned material such as living tissue is not suctioned from the distal end of the suction path 19.

FIG. 8 is a flowchart illustrating the suction action of the suction ON mode. As shown in FIG. 8, in order to perform suction in the suction ON mode, the amount of suction by the suction unit 7 per second is first set by the control unit 5 within a range greater than or equal to the second standard suction amount B2 (step S121).

As the amount of suction by the suction unit 7 is controlled to be greater than or equal to the first standard suction amount B1 in the suction ON mode, all the liquid, which has flowed from the liquid supply unit 6, flows into the suction path 19 via the communication path 22 (step S122). All the liquid, which has flowed into the suction path 19, is suctioned by the suction unit 7, and collected in the collection tank 18 (step S123). That is, all the liquid, which has flowed from the liquid supply unit 6, is suctioned by the suction unit through the communication path 22 and the suction path 19 in order.

As the amount of suction by the suction unit 7 is greater than the second standard suction amount B2 in the suction ON mode, the suction force at the distal end of the suction path 19 is greater than that in the standby mode. As a result, the suctioned material such as living tissue is suctioned at the distal end of the suction path 19 (step S124). The suctioned material, which has been suctioned, is suctioned by the suction unit 7 via the suction path 19, and collected in the collection tank 18 (step S125).

As described above, in the liquid-supply OFF mode, the control unit 5 controls the amount of suction by the suction unit 7 within a range greater than or equal to the first standard suction amount (standard suction amount) B1 between the standby mode and the suction ON mode in accordance with the switching operation in the suction mode input switch 25. That is, the amount of suction by the suction unit 7 is greater than or equal to the first standard suction amount B1 and smaller than the second standard suction amount B2 in the standby mode, and the amount of suction by the suction unit 7 is greater than or equal to the second standard suction amount B2 in the suction ON mode. Thus, in the standby mode, the suction force at the distal end of the suction path 19 does not become great enough to be able to suction the suctioned material such as living tissue. On the other hand, in the suction ON mode, the suction force at the distal end of the suction path 19 is greater than that in the standby mode, and the suctioned material such as living tissue is suctioned at the distal end of the suction path 19. That is, the amount of suction by the suction unit 7 is controlled between the standby mode and the suction ON mode to adjust the suction force at the distal end of the suction path 19.

When the suction action in the suction ON mode is completed, the operation of switching to the standby mode is performed by the suction mode input switch 25 as shown in FIG. 3 (step S109). The process then moves to step S110.

When the treatment is finished in step S110 (step S110—Yes), the medical liquid supply device 1 is powered OFF by the power switch 29 of the input unit 8 (step S111). When the treatment is not finished in step S110 (step S110—No), the process then moves back to step S103 to wait in the standby mode.

Accordingly, the medical liquid supply device 1 having the configuration described above provides the following advantageous effects. That is, in the medical liquid supply device 1 according to the present embodiment, the liquid flows from the liquid supply unit 6 to the liquid supply path 15 in the flow amount per second greater than or equal to the standard flow amount U0 even in the liquid-supply OFF mode. Therefore, the liquid supply path 15 constantly has no parts lacking the liquid up to the communication path 22 in the liquid supply direction in the liquid-supply OFF mode as well. Thus, the liquid can be stably supplied from the distal end of the liquid supply path 15 without the need for much time by the operation of switching to the liquid-supply ON mode in the liquid supply mode input switch 23. That is, the liquid can be stably supplied from the distal end of the liquid supply path 15 with high response.

In the medical liquid supply device 1, the control unit 5 controls the amount of suction by the suction unit 7 between the liquid-supply OFF mode and the liquid-supply ON mode in accordance with the switching operation in the liquid supply mode input switch 23. Thus, in the liquid-supply OFF mode, all the liquid, which has flowed from the liquid supply unit 6, flows into the suction path 19 via the communication path 22. On the other hand, in the liquid-supply ON mode, at least part of the liquid, which has flowed from the liquid supply unit 6, does not flow into the suction path 19 via the communication path 22. That is, the amount of suction by the suction unit 7 is controlled between the liquid-supply OFF mode and the liquid-supply ON mode to adjust the flow amount of the liquid flowing into the suction path 19. As described above, the liquid supply from the distal end of the liquid supply path 15 can be prevented even if the liquid flows from the liquid supply unit 6 to the liquid supply path 15 in the flow amount greater than or equal to the standard flow amount U0 in the liquid-supply OFF mode.

In the medical liquid supply device 1, in the liquid-supply OFF mode, the control unit 5 controls the amount of suction by the suction unit 7 within the range greater than or equal to the first standard suction amount (standard suction amount) B1 between the standby mode and the suction ON mode in accordance with the switching operation in the suction mode input switch 25. Thus, in the standby mode, the suction force at the distal end of the suction path 19 does not become great enough to be able to suction the suctioned material such as living tissue. On the other hand, in the suction ON mode, the suction force at the distal end of the suction path 19 is greater than that in the standby mode, and the suctioned material such as living tissue is suctioned at the distal end of the suction path 19. In this way, the amount of suction by the suction unit 7 is controlled within the range greater than or equal to the first standard suction amount B1 to adjust the suction force at the distal end of the suction path 19. This allows the switch between the standby mode and the suction ON mode to be made in the liquid-supply OFF mode.

In the medical liquid supply device 1, in the liquid-supply ON mode, the control unit 5 controls the amount of suction by the suction unit 7 per second within the range smaller than the first standard suction amount B1. As a result, the flow amount of the liquid flowing from the liquid supply path 15 into the suction path 19 via the communication path 22 is adjusted, and the amount of the liquid supplied from the distal end of the liquid supply path 15 can be adjusted in the liquid-supply ON mode.

Modifications of First Embodiment

The liquid supply amount from the distal end of the liquid supply path 15 in the liquid-supply ON mode is not exclusively adjusted by the configuration according to the first embodiment. FIG. 9 is a flowchart illustrating a liquid supply action of the medical liquid supply device 1 according to a first modification in the liquid-supply ON mode.

As shown in FIG. 9, in order to supply a liquid in the liquid-supply ON mode (step S105 in FIG. 4), the amount of suction by the suction unit 7 per second is first controlled by the control unit 5 to a constant suction amount B5 smaller than the first standard suction amount B1 (step S126).

A liquid supply amount from the distal end of the liquid supply path 15 per second is then input by the liquid supply amount input section 28 of the input unit 8 (step S127). In accordance with the input liquid supply amount, the flow amount from the liquid supply unit 6 to the liquid supply path 15 per second is controlled by the control unit 5 within the range greater than or equal to the standard flow amount U0 (step S128). As the constant suction amount B5 is smaller than the first standard suction amount B1, at least part of the liquid, which has flowed from the liquid supply unit 6, does not flow into the suction path 19 via the communication path 22. The liquid, which does not flow into the suction path 19, is supplied to, for example, living tissue from the distal end of the liquid supply path 15 (step S129).

In this modification, the amount of suction by the suction unit 7 is the constant suction amount B5 in the liquid-supply ON mode. For example, the flow amount from the liquid supply unit 6 is set to a first practice flow amount U3 greater than or equal to the standard flow amount U0. In this case, the flow amount of the liquid flowing from the liquid supply unit 6 into the suction path 19 is a flow amount V'1, and the amount of the liquid supplied from the distal end of the liquid supply path 15 is a first liquid supply amount W'1. The flow amount from the liquid supply unit 6 is decreased from the first practice flow amount U3 to a second practice flow amount U4 within the range greater than or equal to the standard flow amount U0. As the amount of suction by the suction unit 7 is the constant suction amount B5, the flow amount of the liquid flowing from the liquid supply unit 6 into the suction path 19 remains the flow amount V'1 even if the liquid flows in the second practice flow amount U4. However, the second practice flow amount U4 is smaller than the first practice flow amount U3, so that the liquid supply amount of the liquid flowing from the liquid supply unit 6 and supplied from the distal end of the liquid supply path 15 is a second liquid supply amount W'2 smaller than the first liquid supply amount W'1. That is, in the liquid-supply ON mode, the amount of suction by the suction unit 7 is set to the constant suction amount B5 smaller than the first standard suction amount B1, and flow amount from the liquid supply unit 6 is controlled within the range greater than or equal to the standard flow amount U0. Thus, the amount of the liquid supplied from the distal end of the liquid supply path 15 is adjusted.

As in the first embodiment, in the medical liquid supply device 1, the liquid flows from the liquid supply unit 6 to the liquid supply path 15 in the flow amount per second greater than or equal to the standard flow amount U0 in the liquid-supply OFF mode including the standby mode as well. Therefore, the liquid supply path 15 constantly has no parts lacking the liquid up to the communication path 22 in the liquid supply direction in the liquid-supply OFF mode as well. Thus, the liquid is stably supplied from the distal end of the liquid supply path 15 without the need for much time by the operation of switching to the liquid-supply ON mode in the liquid supply mode input switch 23. That is, the liquid is stably supplied from the distal end of the liquid supply path 15 with high response.

Figure 10:
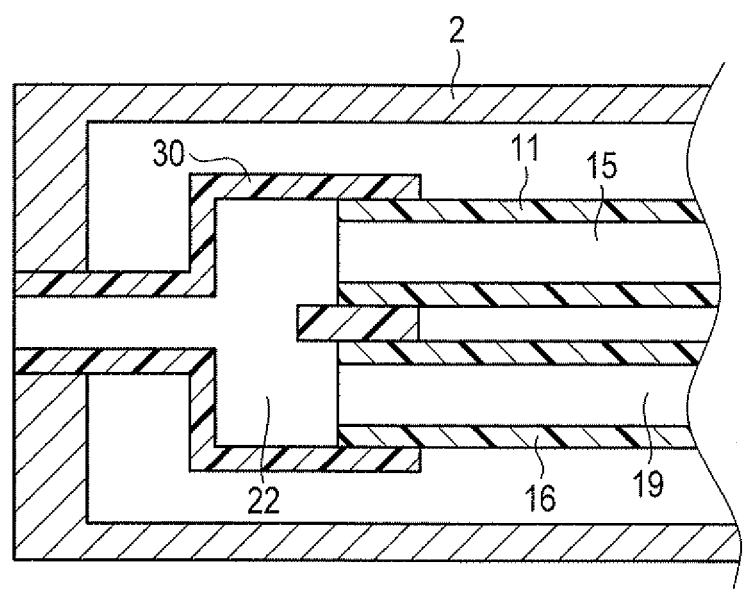
FIG. 10 is a schematic sectional view showing an internal configuration of an insertion section of a medical liquid supply device according to a second modification of the first embodiment.

Although the communication path 22 is defined by the intermediary member 21 in the first embodiment, the present invention is not limited thereto. For example, as a second modification, the distal end of the liquid supply tube 11 and the distal end of the suction tube 16 are connected to a proximal end of a coupling tube 30, as shown in FIG. 10. A distal end of the coupling tube 30 extends to the distal end of the insertion section 2. In this modification, the communication path 22 configured to allow communication between the distal portion of the liquid supply path 15 and the distal portion of the suction path 19 is defined by the coupling tube 30. That is, the coupling tube 30 serves as the third path defining portion which defines the communication path 22.

As described above, according to the second modification, the medical liquid supply device 1 has only to include the first path defining portion which defines the liquid supply path 15, the second path defining portion which defines the suction path 19, and the third path defining portion which defines the communication path 22 configured to allow communication between the liquid supply path 15 and the suction path 19.

Second Embodiment

Now, a second embodiment of the present invention is described with reference to FIG. 11 and FIG. 21. In the second embodiment, the configuration according to the first embodiment is modified as described below. The same parts as those according to the first embodiment are provided with the same reference marks and are not described.

Figure 11:
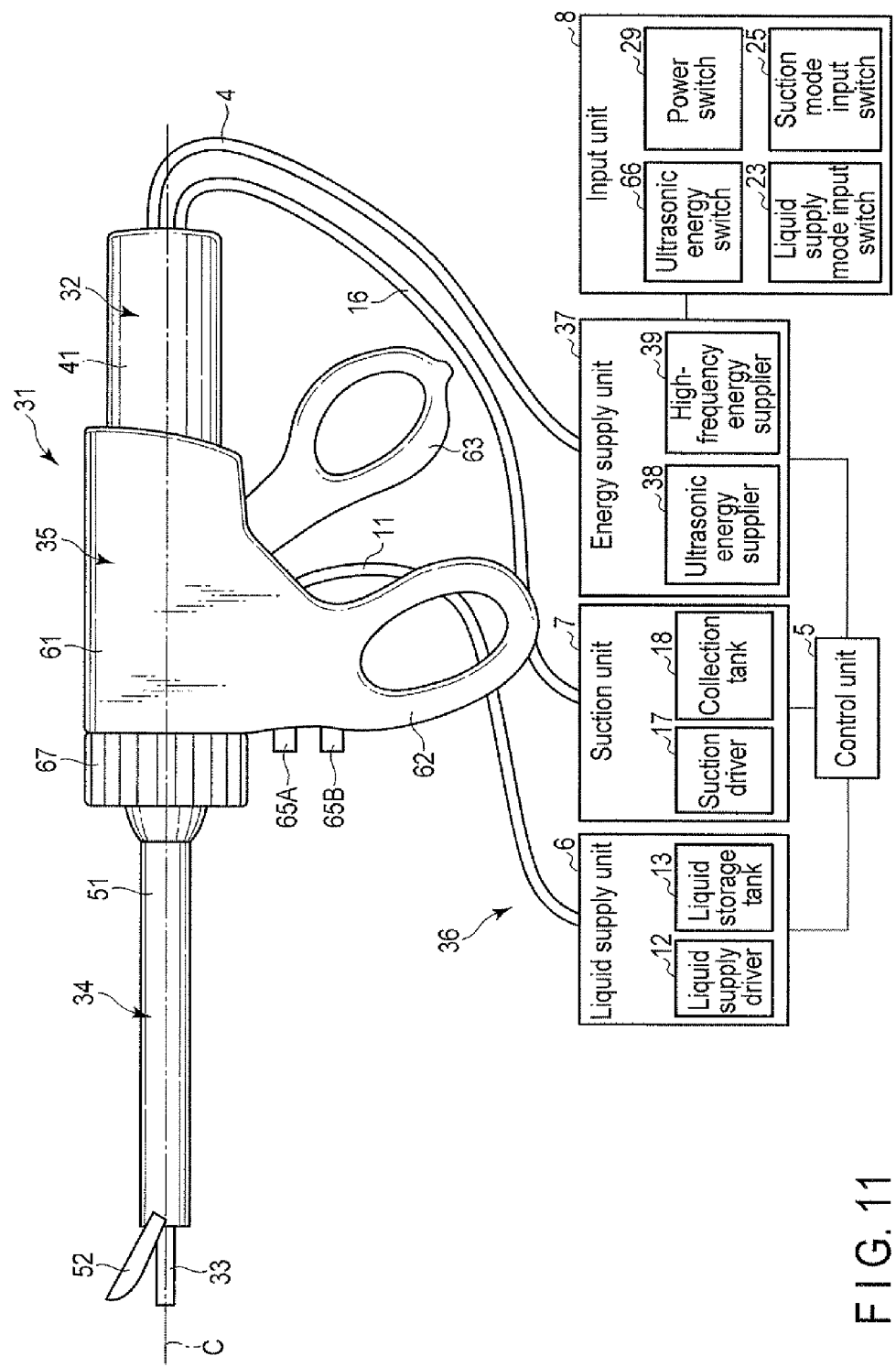
FIG. 11 is a schematic diagram showing a medical treatment according to a second embodiment of the present invention.

FIG. 11 is a diagram showing a medical treatment device 31 according to the present embodiment. The medical treatment device 31 is a bipolar forceps which uses an ultrasonic probe 33 (described later) and a jaw 52 (described later) as electrodes to treat living tissue by a high-frequency current. The medical treatment device 31 is also used as an ultrasonic suction device to selectively shatter and resect living tissue by cavitation caused by liquid supply and ultrasonic vibrations, and to suction the resected living tissue. As shown in FIG. 11, the medical treatment device 31 includes a vibrator unit 32, the ultrasonic probe 33, a sheath unit 34, and a handle unit 35. The medical treatment device 31 is also provided with a medical liquid supply device 36 which includes a liquid supply unit 6 and a suction unit 7 similar to those in the first embodiment.

The vibrator unit 32 includes a vibrator case 41. One end of a cable 4 is connected to a proximal end of the vibrator housing 41. The other end of the cable 4 is connected to an energy supply unit 37. The energy supply unit 37 includes an ultrasonic energy supplier 38, and a high-frequency energy supplier 39. The energy supply unit 37 is electrically connected to a control unit 5. The control unit 5 is electrically connected to the liquid supply unit 6, the suction unit 7, and the input unit 8, as in the first embodiment.

FIG. 12 is a diagram showing a configuration of the vibrator unit 32. As shown in FIG. 12, an ultrasonic vibrator 42 which includes a piezoelectric element configured to convert a current to ultrasonic vibrations is provided inside the vibrator case 41. One end of each of electrical signal lines 43A and 43B is connected to the ultrasonic vibrator 42. The other end of each of the electrical signal lines 43A and 43B is connected to the ultrasonic energy supplier 38 of the energy supply unit 37 through the inside of the cable 4. Ultrasonic vibrations are generated in the ultrasonic vibrator 42 by supplying a current to the ultrasonic vibrator 42 from the ultrasonic energy supply 38 via the electrical signal lines 43A and 43B. A horn 45 which is configured to increase the amplitude of the ultrasonic vibrations is coupled to the distal direction side of the ultrasonic vibrator 42. The horn 45 is attached to the vibrator case 41, and electrically insulated from the vibrator case 41. In the ultrasonic vibrator 42 and the horn 45, a space portion 46 is formed about a longitudinal axis C. In addition to the electrical signal lines 43A and 43B, an electrical signal line 47 extending from the high-frequency energy supplier 39 of the energy supply unit 37 through the inside the cable 4 is connected to the ultrasonic vibrator 42.

FIG. 13 is a diagram showing a configuration of the ultrasonic probe 33. As shown in FIG. 13, the ultrasonic probe 33 is attached to the distal direction side of the horn 45. When the ultrasonic probe 33 is attached to the horn 45, the ultrasonic vibrations generated in the ultrasonic vibrator 42 are transmitted from a proximal end of the ultrasonic probe 33 to a distal end thereof. Cavitation is caused by the transmission of the ultrasonic vibrations to the distal end of the ultrasonic probe 33. Living tissue having low elasticity such as a hepatic cell is selectively shattered and resected by the cavitation. In this case, living tissue having high elasticity such as a blood vessel is not resected by the cavitation.

When the ultrasonic probe 33 is attached to the horn 45, a probe side current path of the high-frequency current is formed from the high-frequency energy supplier 39 to a distal portion of the ultrasonic probe 33 through the electrical signal line 47, the ultrasonic vibrator 42, and the horn 45. Thus, the high-frequency current supplied from the high-frequency energy supplier 39 is transmitted from the proximal end of the ultrasonic probe 33 to the distal end thereof. That is, the ultrasonic probe 33 serves as an energy transmitter capable of transmitting treatment energy such as the high-frequency current and the ultrasonic vibrations from the proximal end to the distal end. The energy supply unit 37 is configured to supply the treatment energy transmitted by the ultrasonic probe 33.

As shown in FIG. 13, a space portion 49 is formed inside the ultrasonic probe 33 from the proximal end to the distal end along the longitudinal axis C. When the ultrasonic probe 33 is attached to the horn 45, a proximal end of the space portion 49 is in communication with the space portion 46 inside the ultrasonic vibrator 42 and the horn 45. As shown in FIG. 12, one end of a suction tube 16 is connected to the space portion 46. As shown in FIG. 11, the suction tube 16 extends to an outside of the vibrator case 41, and the other end of the suction tube 16 is connected to the suction unit 7. The space portion 49, the space portion 46, and an inside of the suction tube 16 serve as a suction path 19 which is configured to pass a suctioned material and a liquid to the suction unit 7. That is, an inner peripheral portion of the ultrasonic probe 33 is a part of a path defining portion (second path defining portion) which defines the suction path 19. The suctioned material such as living tissue resected by cavitation is suctioned from the distal end of the suction path 19.

Figure 14:
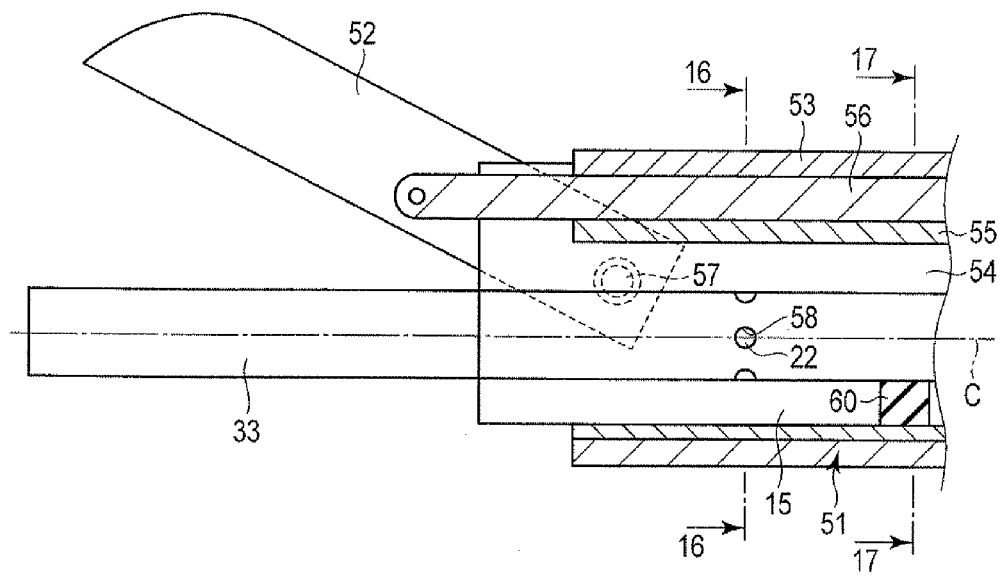
FIG. 14 is a schematic sectional view showing a state in which the ultrasonic probe is inserted through a sheath according to the second embodiment.

As shown in FIG. 11, the sheath unit 34 includes a sheath 51 through which the ultrasonic probe 33 is inserted, and the jaw 52 attached to a distal portion of the sheath 51. FIG. 14 is a diagram showing a state in which the ultrasonic probe 33 is inserted through the sheath 51. As shown in FIG. 14, the sheath 51 includes an outer pipe 53, and an inner pipe 55. A movable member 56 is provided between the outer pipe 53 and the inner pipe 55. The jaw 52 is attached to a distal portion of the outer pipe 53 via a linking screw 57.

A distal end of the movable member 56 is coupled to the jaw 52. The jaw 52 is rotated relative to the sheath 51 around the linking screw 57 by the movement of the movable member 56 along the longitudinal axis C. In this way, the jaw 52 opens/closes relative to the distal portion of the ultrasonic probe 33. As the jaw 52 opens/closes relative to the distal portion of the ultrasonic probe 33, the living tissue, for example, can be grasped between the distal portion of the ultrasonic probe 33 and the jaw 52. When the ultrasonic probe 33 is inserted through the sheath 51, a space portion 54 is formed between an outer peripheral portion of the ultrasonic probe 33 and the inner pipe 55 of the sheath 51.

Figure 15:
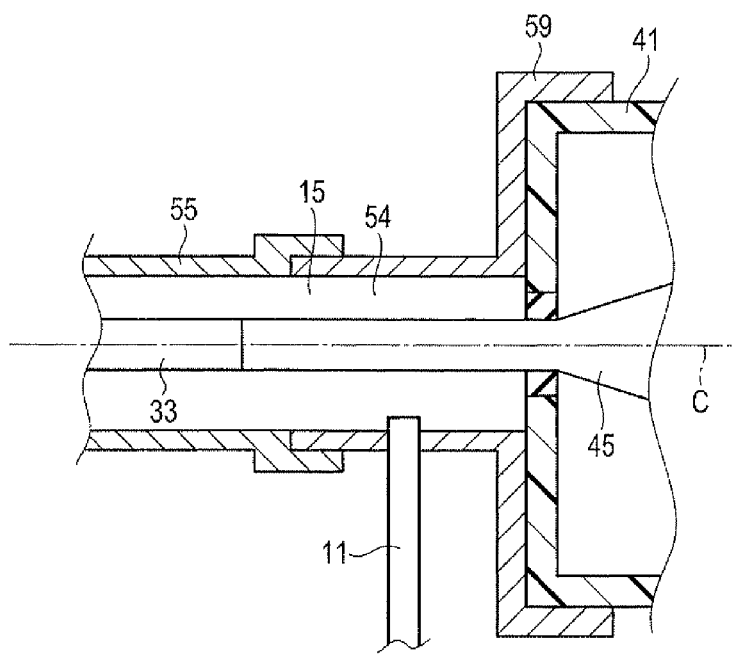
FIG. 15 is a schematic sectional view showing a configuration of a coupling portion between the sheath and a vibrator case according to the second embodiment.

FIG. 15 is a schematic diagram showing the configuration of a coupling portion between the sheath 51 and the vibrator case 41. A distal portion of a cylindrical intermediary member 59 is attached to a proximal portion of the inner pipe 55 of the sheath 51. The sheath 51 is rotatable relative to the intermediary member 59 around the longitudinal axis C. A distal portion of the vibrator case 41 is attached to a proximal portion of the intermediary member 59.

The space portion 54 formed between the ultrasonic probe 33 and the sheath 51 extends to a distal face of the vibrator case 41. One end of a liquid supply tube 11 is connected to an inside of the intermediary member 59. As shown in FIG. 11, the liquid supply tube 11 extends to an outside of the handle unit 35, and the other end of the liquid supply tube 11 is connected to the liquid supply unit 6. An inside of the liquid supply tube 11 and the space portion 54 serve as a liquid supply path 15 which is configured to pass the liquid flowing from the liquid supply unit 6. That is, the outer peripheral portion of the ultrasonic probe 33 and the inner peripheral portion of the sheath 51 is a part of a path defining portion (first path defining portion) which defines the liquid supply path 15.

As shown in FIG. 13 and FIG. 14, a path defining surface 58 which defines a communication path 22 configured to allow communication between the distal portion of the liquid supply path 15 and the distal portion of the suction path 19 is provided in the ultrasonic probe 33. That is, the path defining surface 58 serves as a path defining portion (third path defining portion) which defines the communication path 22. The path defining surface 58 is provided in a part of the ultrasonic probe 33 to the proximal direction side of a distal end of the sheath 51.

FIG. 16 is a sectional view taken along line 16-16 of FIG. 14. As shown in FIG. 16, a plurality of communication paths 22 are provided apart from one another around the longitudinal axis C.

An electrical signal line (not shown) extending from the high-frequency energy supplier 39 of the energy supply unit 37 through the inside of the cable 4 is connected to the vibrator case 41. The vibrator case 41 and the intermediary member 59 include electrically conducting portions (not shown) configured to electrically connect the electrical signal line from the high-frequency energy supplier 39 to the sheath 51. Accordingly, a jaw side current path of the high-frequency current is formed from the high-frequency energy supplier 39 to the jaw 52 through the electrically conducting portion of the vibrator case 41 and the sheath 51. The ultrasonic vibrator 42 and the horn 45 are insulated from the vibrator case 41.

As shown in FIG. 14, an insulating member 60 is attached to the outer peripheral portion of the ultrasonic probe 33 by a rubber lining. The insulating member 60 is located at a node position of ultrasonic vibrations. The ultrasonic probe 33 is supported by the sheath 51 via the insulating member 60. By the provision of the insulating member 60, the contact between the ultrasonic probe 33 and the inner pipe 55 of the sheath 51 is prevented, and the ultrasonic probe 33 is insulated from the sheath 51. Insulating coating is preferably provided in an inner peripheral surface of the inner pipe 55. This also effectively prevents the electrical conduction between the ultrasonic probe 33 and the sheath 51 via the liquid passing through the liquid supply path 15.

FIG. 17 is a sectional view taken along line 17-17 of FIG. 14. As shown in FIG. 17, the insulating member 60 is only attached over a predetermined angular range of the outer peripheral portion of the ultrasonic probe 33 around the longitudinal axis C. That is, the insulating member 60 is not attached all around the outer peripheral portion of the ultrasonic probe 33. Therefore, the liquid can pass through a part where the insulating member 60 is located in directions parallel to the longitudinal axis C.

Figure 18:
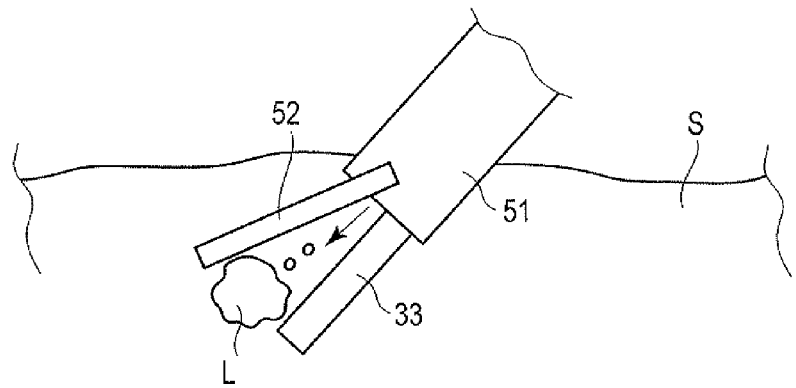
FIG. 18 is a schematic view showing one example of a treatment conducted by using a high-frequency current in the medical treatment device according to the second embodiment.

A treatment using the high-frequency current is conducted by the jaw 52 and the distal portion of the ultrasonic probe 33. FIG. 18 is a diagram showing one example of a treatment conducted by the use of the high-frequency current in the medical treatment device 31. As shown in FIG. 18, the medical treatment device 31 treats living tissue S by the high-frequency current while a constant amount of a liquid L such as a physiological saline solution is being supplied from the distal end of the liquid supply path 15 of the medical liquid supply device 36. In this case, the jaw 52 and the ultrasonic probe 33 are in contact with the living tissue S while the jaw 52 is open relative to the distal portion of the ultrasonic probe 33. The liquid L is supplied to a part of a surface of the living tissue S between the jaw 52 and the ultrasonic probe 33. In this condition, a high-frequency current is supplied to the probe side current path and the jaw side current path from the high-frequency energy supplier 39. As a result, the high-frequency current runs through the living tissue S between the jaw 52 and the ultrasonic probe 33 via the supplied liquid L. The living tissue S is reformed by the high-frequency current, and is coagulated. In this way, the living tissue S is coagulated over a wide range between the jaw 52 opened relative to the ultrasonic probe 33 and the ultrasonic probe 33.

As shown in FIG. 11, the handle unit 35 includes a cylindrical casing 61, a fixed handle 62 provided integrally with the cylindrical casing 61, and a movable handle 63 configured to open/close relative to the fixed handle 62. The cylindrical casing 61 is attached to the vibrator case 41, and is made of an insulating material. The movable handle 63 is coupled, via an intermediary member (not shown), to the movable member 56 provided to the sheath 51. The movable handle 63 is opened/closed relative to the fixed handle 62, and the movable member 56 thereby moves along the longitudinal axis C. Thus, the jaw 52 opens/closes relative to the distal portion of the ultrasonic probe 33.

Two switches 65A and 65B are provided to the fixed handle 62. The switches 65A and 65B are electrically connected to the energy supply unit 37, for example, via electrical signal line (not shown) passing through the inside of the cable 4. As the energy supply unit 37 is electrically connected to the control unit 5, the switches 65A and 65B are electrically connected to the control unit 5. When the switch 65A is pressed, it enters a first energy mode in which to the ultrasonic probe 33 transmit the high-frequency current supplied from the high-frequency energy supplier 39. For example, the first energy mode is an energy mode used during the treatment by the high-frequency current shown in FIG. 18.

On the other hand, when the switch 65B is pressed, it enters a second energy mode in which no high-frequency current is supplied from the high-frequency energy supplier 39. That is, the switches 65A and 65B are high-frequency energy switches configured to switch an energy mode of the energy supply unit 37 to the first energy mode or the second energy mode. A switch to the first energy mode or the second energy mode is only made in the liquid-supply ON mode in which the liquid is supplied from the distal end of the liquid supply path 15. Therefore, the switch to the first energy mode or the second energy mode is not made in the liquid-supply OFF mode in which the liquid is not supplied from the distal end of the liquid supply path 15.

The input unit 8 includes an ultrasonic energy switch 66. By a switching operation in the ultrasonic energy switch 66, a current is supplied to the ultrasonic vibrator 42 from the ultrasonic energy supplier 38 via the electrical signal lines 43A and 43B. As a result, ultrasonic vibrations are generated in the ultrasonic vibrator 42. As described above, the switches 65A and 65B and the ultrasonic energy switch 66 serve as energy mode input sections configured to switch the energy mode of treatment energy such as the ultrasonic vibrations and the high-frequency current supplied from the energy supply unit 37. The input unit 8 also includes a liquid supply mode input switch 23, which is a liquid supply mode input section, and a suction mode input switch 25, which is a suction mode input section. As in the first embodiment, the liquid supply mode input switch 23 is configured to switch the liquid supply mode between the liquid-supply ON mode and the liquid-supply OFF mode. As in the first embodiment, the suction mode input switch 25 is configured to switch the suction mode between the standby mode and the suction ON mode. In the present embodiment, the input unit 8 is not provided with the liquid supply amount input section 28.

A rotational operation knob 67 is coupled to the distal direction side of the cylindrical casing 61. The rotational operation knob 67 is rotatable relative to the cylindrical casing 61 around the longitudinal axis C. The rotational operation knob 67 is made of an insulating material. The sheath 51 is attached to an inner peripheral side of the rotational operation knob 67. If the rotational operation knob 67 is rotated, the ultrasonic probe 33, the sheath 51, and the jaw 52 rotate around the longitudinal axis C together with the rotational operation knob 67.

Now, the functions of the medical treatment device 31 are described. The liquid supply action and the suction action of the medical liquid supply device 36 of the medical treatment device 31 are similar to those of the medical liquid supply device 1 according to the first embodiment except for the liquid supply action in the liquid-supply ON mode (step S105). Therefore, the liquid supply action in the liquid-supply ON mode is only described below.

Figure 19:
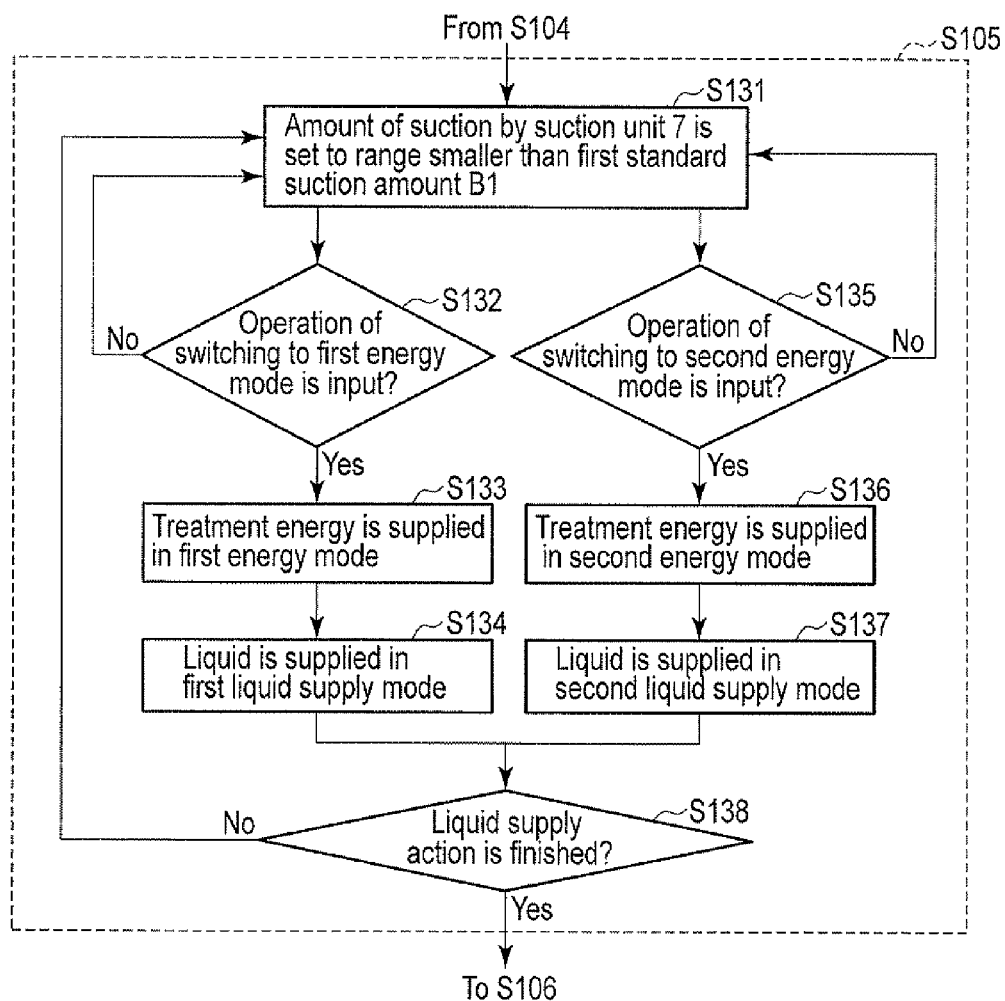
FIG. 19 is a flowchart illustrating a liquid supply action of the medical treatment device according to the second embodiment in a liquid-supply ON mode.

FIG. 19 is a flowchart illustrating a liquid supply action of the medical treatment device 31 in the liquid-supply ON mode. As shown in FIG. 19, when the liquid supply mode is switched to the liquid-supply ON mode by the liquid supply mode input switch 23 of the input unit 8 (step S104—Yes in FIG. 4), the amount of suction by the suction unit 7 per second is set by the control unit 5 to the range smaller than the first standard suction amount B1 (step S131). Here, the range smaller than the first standard suction amount B1 includes the case in which a suction driver 17 of the suction unit 7 is stopped and the suction force of the suction unit 7 is zero. In the liquid-supply ON mode, the amount of suction by the suction unit 7 is smaller than the first standard suction amount B1. Therefore, as in the first embodiment, at least part of the liquid, which has flowed from the liquid supply unit 6, does not flow into the suction path 19 via the communication path 22. The liquid, which does not flow into the suction path 19, is supplied to, for example, living tissue from the distal end of the liquid supply path 15.

As in the first embodiment, in the medical liquid supply device 36 of the medical treatment device 31, the liquid flows from the liquid supply unit 6 to the liquid supply path 15 in a flow amount per second greater than or equal to the standard flow amount U0 in the liquid-supply OFF mode including the standby mode as well. Therefore, the liquid supply path 15 constantly has no parts lacking the liquid up to the communication path 22 in the liquid supply direction in the liquid-supply OFF mode as well. Thus, the liquid is stably supplied from the distal end of the liquid supply path 15 without the need for much time by the operation of switching to the liquid-supply ON mode in the liquid supply mode input switch 23. That is, the liquid is stably supplied from the distal end of the liquid supply path 15 with high response.

In the medical treatment device 31, the energy mode of the energy supply unit 37 is switched to the first energy mode by pressing the switch 65A (step S132—Yes). As a result, treatment energy is supplied from the energy supply unit 37 in the first energy mode (step S133). In the first energy mode, a high-frequency current is supplied from the high-frequency energy supplier 39, and the high-frequency current is transmitted by the ultrasonic probe 33.

The liquid supply action is then performed in a first liquid supply mode (step S134). FIG. 20 is a flowchart illustrating the liquid supply action in the first liquid supply mode. As shown in FIG. 20, in the first liquid supply mode, the amount of suction by the suction unit 7 is set to a first practice suction amount B7 smaller than the first standard suction amount B1 (step S141). In this case, the liquid flowing from the liquid supply unit 6 flows into the suction path 19 through the communication path 22 in a first flow amount V3 (step S142). The liquid, which does not flow into the suction path 19, is supplied from the distal end of the liquid supply path 15 in a first liquid supply amount W3 (step S143).

As described above, when the energy mode is switched to the first energy mode, the amount of suction by the suction unit 7 is controlled by the control unit 5 to set the first liquid supply mode. As shown in FIG. 18, a treatment by the high-frequency current is conducted while a liquid L such as a physiological saline solution is being supplied to the living tissue S between the jaw 52 opened relative to the ultrasonic probe 33 and the ultrasonic probe 33. The living tissue S is reformed by the high-frequency current, and is coagulated. Thus, the living tissue S is coagulated over the wide range between the jaw 52 opened relative to the ultrasonic probe 33 and the ultrasonic probe 33. In this case, the first liquid supply amount W3 from the distal end of the liquid supply path 15 per second is constant and small. When the liquid supply action in the first liquid supply mode is completed, the process then moves to step S138.

The energy mode of the energy supply unit 37 is switched to the second energy mode by pressing the switch 65B (step S135—Yes). As a result, treatment energy is supplied from the energy supply unit 37 in the second energy mode (step S136). In the second energy mode, a high-frequency current is not supplied from the high-frequency energy supplier 39.

The liquid supply action is then performed in a second liquid supply mode (step S137). FIG. 21 is a flowchart illustrating the liquid supply action in the second liquid supply mode. As shown in FIG. 21, in the second liquid supply mode, the amount of suction by the suction unit 7 is set to a second practice suction amount B8 smaller than the first practice suction amount B7 (step S145). In this case, the liquid flowing from the liquid supply unit 6 flows into the suction path 19 through the communication path 22 in a second flow amount V4 smaller than the first flow amount V3 (step S146). The liquid, which does not flow into the suction path 19, is supplied from the distal end of the liquid supply path 15 in a second liquid supply amount W4 greater than the first liquid supply amount W3 (step S147). The second practice suction amount B8 may be zero. In this case, the second flow amount V4 is zero, and all the liquid, which has flowed from the liquid supply unit 6, is supplied from the distal end of the liquid supply path 15.

As described above, when the energy mode is switched to the second energy mode, the amount of suction by the suction unit 7 is controlled by the control unit 5 to set the second liquid supply mode. The high-frequency current is not supplied in the second energy mode, and the amount of the liquid supplied from the distal end of the liquid supply path 15 is greater in the second liquid supply mode than that in the first liquid supply mode. Thus, a bleeding part is checked by the use of the liquid supplied from the distal end of the liquid supply path 15. When the liquid supply action in the second liquid supply mode is completed, the process then moves to step S138.

As described above, the control unit 5 controls the amount of suction by the suction unit 7 between the first liquid supply mode and the second liquid supply mode in accordance with the operation of switching the energy mode of the treatment energy supplied from the energy supply unit 37. The flow amount of the liquid flowing from the liquid supply path 15 into the suction path 19 via the communication path 22 is adjusted between the first liquid supply mode and the second liquid supply mode by controlling the amount of suction by the suction unit 7. As a result, the second liquid supply amount W4 from the distal end of the liquid supply path 15 in the second liquid supply mode is greater than the first liquid supply amount W3 from the distal end of the liquid supply path 15 in the first liquid supply mode.

When the liquid supply action is finished in step S138 (step S138—Yes), the process moves to step S106 in FIG. 3. On the other hand, when the liquid supply action is not finished in step S138 (step S138—No), the process moves back to step S131.

Accordingly, the medical treatment device 31 having the configuration described above provides the following advantageous effects in addition to the advantageous effects similar to those according to the first embodiment. That is, in the medical liquid supply device 36 of the medical treatment device 31 according to the present embodiment, the flow amount of the liquid flowing from the liquid supply path 15 into the suction path 19 via the communication path 22 is adjusted between the first liquid supply mode and the second liquid supply mode by controlling the amount of suction by the suction unit 7. As a result, the second liquid supply amount W4 from the distal end of the liquid supply path 15 in the second liquid supply mode can be greater than the first liquid supply amount W3 from the distal end of the liquid supply path 15 in the first liquid supply mode.

Moreover, in the medical treatment device 31, the control unit 5 controls the amount of suction by the suction unit 7 between the first liquid supply mode and the second liquid supply mode in accordance with the operation of switching the energy mode of the treatment energy supplied from the energy supply unit 37. That is, the liquid supply amount from the distal end of the liquid supply path 15 is adjusted in conformity to the energy mode used in a treatment. Consequently, when a treatment is conducted in a given energy mode, a liquid amount suited to the treatment can be supplied.

Modification of Second Embodiment

According to the second embodiment, the amount of suction by the suction unit 7 is controlled and the liquid supply amount from the distal end of the liquid supply path 15 is adjusted in accordance with the operation of switching the energy mode in the switches 65A and 65B, which are high-frequency energy switches. However, the present invention is not limited thereto. For example, the amount of suction by the suction unit 7 may be controlled and the liquid supply amount from the distal end of the liquid supply path 15 may be adjusted in accordance with the operation of switching the energy mode in the ultrasonic energy switch 66. In this case, the ultrasonic energy switch 66 is used to switch, for example, between a third energy mode (first energy mode) in which ultrasonic vibrations are transmitted by the ultrasonic probe 33 and a fourth energy mode (second energy mode) in which ultrasonic vibrations are not generated. For example, the amount of suction by the suction unit 7 is controlled so that the first liquid supply mode is set when the energy mode is switched to the third energy mode and so that the second liquid supply mode is set when the energy mode is switched to the fourth energy mode. That is, the amount of suction by the suction unit 7 has only to be controlled between a first liquid supply mode and a second liquid supply mode having a greater liquid supply amount than the first liquid supply mode in accordance with the switching operation in an energy mode input section such as the switches 65A and 65B and the ultrasonic energy switch 66.

The medical treatment device 31 may also be used as an ultrasonic coagulation-and-cutting device configured to coagulate and cut living tissue such as a blood vessel grasped between the ultrasonic probe 33 and the jaw 52. In this case, frictional heat is generated between the ultrasonic probe 33 and the living tissue by the ultrasonic vibrations of the ultrasonic probe 33 while the tissue is grasped between the ultrasonic probe 33 and the jaw 52. The living tissue is cut by the generated frictional heat. The living tissue is also reformed by the passage of a high-frequency current through the living tissue between the jaw 52 and the distal portion of the ultrasonic probe 33. As a result, the living tissue is coagulated.

Figure 22:
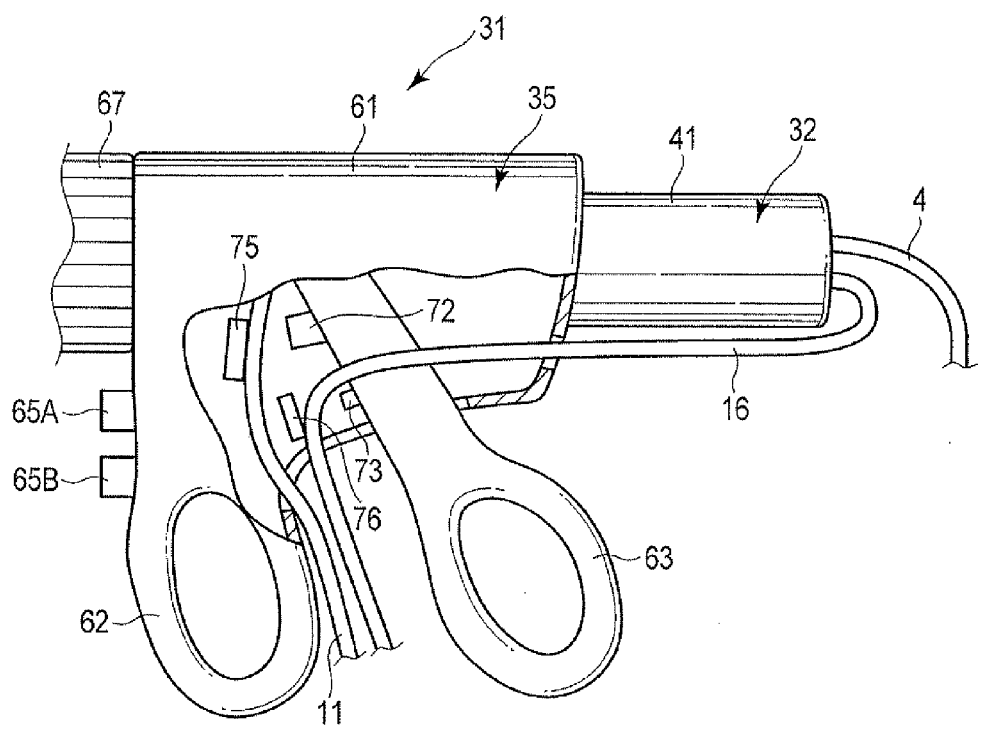
FIG. 22 is a schematic partially sectional side view showing a configuration of a handle unit in a state that a movable handle of a medical treatment device according to a modification of the second embodiment is open relative to a fixed handle.
Figure 23:
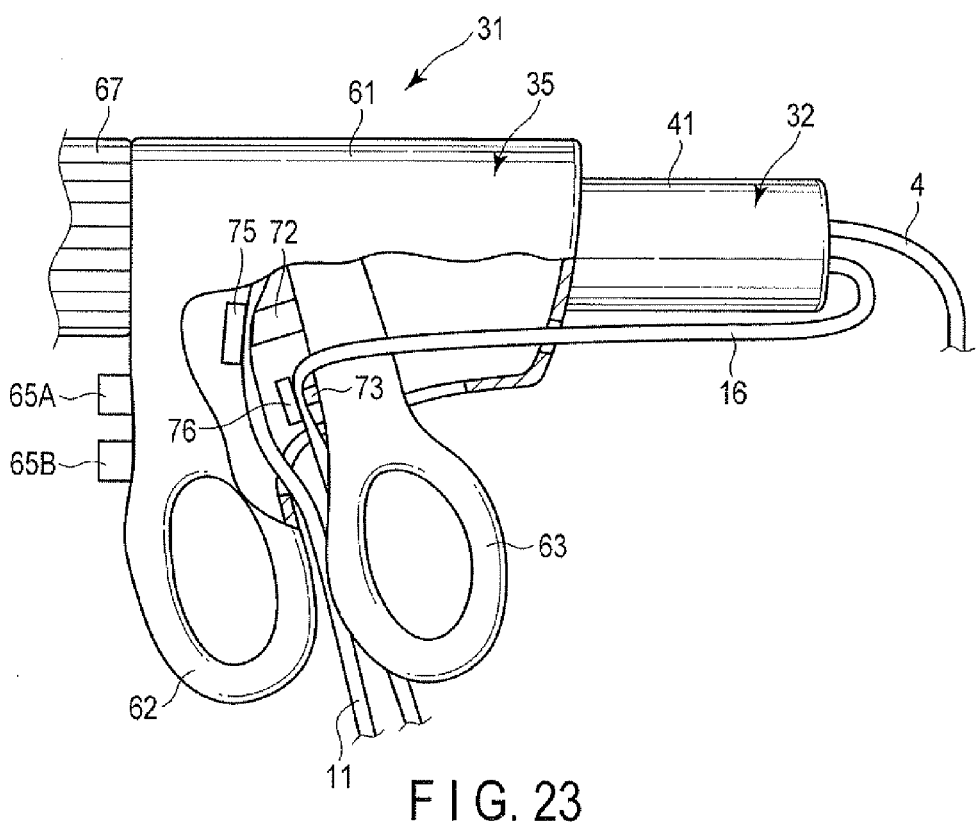
FIG. 23 is a schematic partially sectional side view showing the configuration of the handle unit in a state that the movable handle of the medical treatment device according to the modification of the second embodiment is closed relative to the fixed handle.

The medical treatment device 31 having an ultrasonic coagulation-and-cutting function is shown below as a modification. FIG. 22 and FIG. 23 are schematic diagrams showing a configuration of the handle unit 35 of the medical treatment device 31. As shown in FIG. 22 and FIG. 23, in the medical treatment device 31, the suction tube 16 extending outside the vibrator case 41 passes through the inside of the handle unit 35. The suction tube 16 then extends to the outside of the handle unit 35, and is connected to the suction unit 7. As in the second embodiment, the liquid supply tube 11 extends to the outside of the handle unit 35, and is connected to the liquid supply unit 6.

A first movable member 72 and a second movable member 73 are attached to the movable handle 63. If the movable handle 63 is opened/closed, the first movable member 72 and the second movable member 73 move together with the movable handle 63. A first fixed member 75 and a second fixed member 76 are fixed to the inside of the handle unit 35. The liquid supply tube 11 runs between the first movable member 72 and the first fixed member 75 inside the handle unit 35. The suction tube 16 runs between the second movable member 73 and the second fixed member 76 inside the handle unit 35.

As shown in FIG. 23, if the movable handle 63 is closed relative to the fixed handle 62, the liquid supply tube 11 is sandwiched between the first movable member 72 and the first fixed member 75. As a result, the liquid supply path 15 is blocked at a position where the liquid supply path 15 is sandwiched, and the liquid is not supplied from the distal end of the liquid supply path 15. Moreover, if the movable handle 63 is closed relative to the fixed handle 62, the suction tube 16 is sandwiched between the second movable member 73 and the second fixed member 76. As a result, the suction path 19 is blocked at a position where the suction tube 16 is sandwiched, and suction from the distal end of the suction path 19 is not performed.

The living tissue is ultrasonically coagulated and cut between the jaw 52 and the ultrasonic probe 33 by closing the movable handle 63 relative to the fixed handle 62 in a state that the jaw 52 is closed relative to the distal portion of the ultrasonic probe 33. When a liquid is supplied from the distal end of the liquid supply path 15 during the ultrasonic coagulation-and-cutting treatment, the temperature is reduced by the liquid supply. Thus, frictional heat is not easily generated, and the performance of the treatment of cutting the living tissue deteriorates. When suction from the distal end of the suction path 19 is performed during the ultrasonic coagulation-and-cutting treatment, the living tissue easily adheres to the distal end of the suction path 19. Therefore, the jaw 52 and the distal portion of the ultrasonic probe 33 do not easily move, and workability during the treatment deteriorates.

Thus, in this modification, if the movable handle 63 is closed relative to the fixed handle 62, the liquid supply path 15 is blocked by the first movable member 72 and the first fixed member 75. As a result, the liquid is not supplied from the distal end of the liquid supply path 15. If the movable handle 63 is closed relative to the fixed handle 62, the suction path 19 is blocked by the second movable member 73 and the second fixed member 76. As a result, suction from the distal end of the suction path 19 is not performed.

As described above, in this modification, the liquid supply from the distal end of the liquid supply path 15 and the suction from the distal end of the suction path 19 are not performed when the living tissue is ultrasonically coagulated and cut between the jaw 52 and the ultrasonic probe 33. This can prevent the deterioration in the treatment performance and the deterioration in workability during the ultrasonic coagulation-and-cutting treatment.

Other characteristic technical matters according to the present invention are additionally set forth below.

Notes (Additional Note 1)

A medical treatment device comprising:

an energy transmitter in which a suction path is defined along a longitudinal axis, and which is configured to transmit treatment energy including at least one of a high-frequency current and ultrasonic vibrations from a proximal end to a distal end;

a sheath through which the energy transmitter is inserted, and which defines a liquid supply path along the longitudinal axis between the energy transmitter and thereof;

a path defining portion which is provided in a part of the energy transmitter to a proximal direction side of a distal end of the sheath, and which defines a communication path configured to allow communication between the liquid supply path and the suction path;

a liquid supply unit which is configured to cause a liquid to flow into the liquid supply path in a flow amount greater than or equal to a standard flow amount so that the liquid supply path constantly has no parts lacking the liquid up to the communication path in a liquid supply direction;

a suction unit which configured to perform suction via the suction path; and a control unit which is configured to control an amount of suction by the suction unit to adjust a flow amount of the liquid flowing from the liquid supply path into the suction path via the communication path between a first liquid supply mode and a second liquid supply mode, a liquid supply amount from a distal end of the liquid supply path being greater in the second liquid supply mode than in the first liquid supply mode.

(Additional Note 2)

The medical treatment device according to Additional note 1, further comprising:

an energy supply unit configured to supply the treatment energy transmitted by the energy transmitter; and an energy mode input section configured to switch an energy mode of the treatment energy supplied from the energy supply unit, wherein the control unit is configured to control the amount of suction by the suction unit between the first liquid supply mode and the second liquid supply mode in accordance with a switching operation in the energy mode input section.

(Additional Note 3)

The medical treatment device according to Additional note 2, wherein the energy supply unit includes a high-frequency energy supplier configured to supply the high-frequency current as the treatment energy, the energy mode input section includes a high-frequency energy switch configured to switch the energy mode of the energy supply unit to a first energy mode in which the energy transmitter transmits the high-frequency current supplied from the high-frequency energy supplier or to a second energy mode in which the high-frequency current is not supplied from the high-frequency energy supplier, and the control unit is configured to control the amount of suction by the suction unit in accordance with a switching operation in the high-frequency energy switch so that the first liquid supply mode is set when the energy mode is switched to the first energy mode by the high-frequency energy switch and so that the second liquid supply mode is set when the energy mode is switched to the second energy mode by the high-frequency energy switch.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A medical liquid supply device comprising:

a liquid supply path, the liquid supply path having a distal end to which a liquid is supplied;

a suction path, the suction path having a distal end through which a material is suctioned;

a liquid supply driver which is configured to supply the liquid via the liquid supply path when being driven;

a suction driver which is configured to perform suction via the suction path when being driven;

a communication path having a first end which is communicated with the liquid supply path at a position between the liquid supply driver and the distal end of the liquid supply path, and having a second end which is communicated with the suction path at a position between the suction driver and the distal end of the suction path;

a liquid supply mode input that is configured to select a liquid-supply ON mode in which the liquid is supplied from the distal end of the liquid supply path; and a control unit which is configured to control the liquid supply driver and the suction driver in accordance with whether the liquid-supply ON mode is selected, the control unit being configured to control the liquid supply driver to supply liquid such that liquid flows from the liquid supply driver in the liquid supply path regardless of whether the liquid-supply ON mode is selected, the control unit being configured to control the liquid supply driver and the suction driver such that all the liquid that flows from the liquid supply driver flows into the communication path and is suctioned by the suction driver through the suction path when the liquid-supply ON mode is not selected, and the control unit being configured to control the liquid supply driver and the suction driver such that at least a part of the liquid that flows from the liquid supply driver does not flow into the communication path and is supplied from the distal end of the liquid supply path when the liquid-supply ON mode is selected.

2. The medical liquid supply device according to claim 1, wherein the control unit is configured to control an amount of suction by the suction driver so that a first suction amount when the liquid-supply ON mode is not selected is greater than a second suction amount when the liquid-supply ON mode is selected.

3. The medical liquid supply device according to claim 2, further comprising a suction mode input configured to select a suction mode in which the material is suctioned through the distal end of the suction path when the liquid-supply ON mode is not selected, wherein the control unit is configured to control the amount of suction by the suction driver in accordance with whether the suction mode is selected, the control unit is configured to adjust a suction force at the distal end of the suction path by controlling the amount of suction of the suction driver, when the suction mode is selected, the control unit is configured to adjust the suction amount of the suction driver to a third suction amount which is greater than the first suction amount and the second suction amount.

4. The medical liquid supply device according to claim 2, further comprising a liquid supply amount input configured to input an amount of the liquid supplied from the distal end of the liquid supply path when the liquid-supply ON mode is selected, wherein the control unit is configured to control the amount of suction by the suction driver in accordance with an input from the liquid supply amount input so that a flow amount of the liquid that flows from the liquid supply path into the communication path is adjusted so as to adjust the amount of liquid supplied from the distal end of the liquid supply path.

5. The medical liquid supply device according to claim 2, further comprising a liquid supply amount input configured to input a liquid supply amount from the distal end of the liquid supply path when the liquid-supply ON mode is selected, wherein in the liquid-supply ON mode, the control unit is configured to set the amount of suction by the suction driver to a second suction amount that is less than a first suction amount when the liquid-supply ON mode is not selected, the second suction amount being a constant suction amount, the control unit is configured to control the flow amount from the liquid supply unit within a range greater than or equal to a flow amount when the liquid-supply ON mode is not selected, the flow amount being controlled in accordance with an input in the liquid supply amount input, adjusting the amount of liquid supplied from the distal end of the liquid supply path.

6. The medical liquid supply device according to claim 1, further comprising:

an energy transmitter in which the suction path is defined along a longitudinal axis, and which is configured to transmit treatment energy including at least one of a high-frequency current and ultrasonic vibrations from a proximal end to a distal end; and a sheath through which the energy transmitter is inserted, and which defines the liquid supply path along the longitudinal axis between the energy transmitter and thereof, wherein the communication path is provided in a part of the energy transmitter proximally from a distal end of the sheath, and in the liquid-supply ON mode, the control unit is configured to control the amount of suction by the suction unit to adjust the flow amount of the liquid flowing from the liquid supply path into the suction path via the communication path between a first liquid supply mode and a second liquid supply mode, a liquid supply amount from a distal end of the liquid supply path being greater in the second liquid supply mode than in the first liquid supply mode.

7. The medical liquid supply device according to claim 6, further comprising:

an energy supply unit configured to supply the treatment energy transmitted by the energy transmitter; and an energy mode input section configured to switch an energy mode of the treatment energy supplied from the energy supply unit, wherein the control unit is configured to control the amount of suction by the suction unit between the first liquid supply mode and the second liquid supply mode in accordance with a switching operation in the energy mode input section.

8. The medical liquid supply device according to claim 7, wherein the energy supply unit includes a high-frequency energy supplier configured to supply the high-frequency current as the treatment energy, the energy mode input section includes a high-frequency energy switch configured to switch the energy mode of the energy supply unit to a first energy mode in which the energy transmitter transmits the high-frequency current supplied from the high-frequency energy supplier or to a second energy mode in which the high-frequency current is not supplied from the high-frequency energy supplier, and the control unit is configured to control the amount of suction by the suction unit in accordance with a switching operation in the high-frequency energy switch so that the first liquid supply mode is set when the energy mode is switched to the first energy mode by the high-frequency energy switch and so that the second liquid supply mode is set when the energy mode is switched to the second energy mode by the high-frequency energy switch.

* * * * *